(12) United States Patent
Compan

(10) Patent No.: US 9,168,250 B2
(45) Date of Patent: *Oct. 27, 2015

(54) PHARMACEUTICAL COMPOSITION FOR TREATING AND/OR PREVENTING A PATHOLOGY ASSOCIATED WITH AN OBSESSIONAL BEHAVIOR OR WITH OBESITY

(71) Applicant: Centre National de la Recherche Scientifique—CNRS, Paris (FR)

(72) Inventor: Valerie Compan, Montpellier (FR)

(73) Assignee: Centre National de la Recherche Scientifique-CNRS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,806

(22) Filed: Apr. 3, 2013

(65) Prior Publication Data

US 2013/0274293 A1    Oct. 17, 2013

Related U.S. Application Data

(60) Continuation of application No. 12/256,642, filed on Oct. 23, 2008, now Pat. No. 8,436,021, which is a division of application No. 11/118,745, filed on Apr. 29, 2005, now Pat. No. 8,859,537, which is a continuation of application No. PCT/FR03/03262, filed on Oct. 31, 2003.

(30) Foreign Application Priority Data

Oct. 31, 2002   (FR) ..................... 02 13725

(51) Int. Cl.
*A61K 31/454*   (2006.01)
*A61K 31/445*   (2006.01)
*C07K 14/705*   (2006.01)
*A61K 38/00*    (2006.01)

(52) U.S. Cl.
CPC ............. *A61K 31/445* (2013.01); *A61K 31/454* (2013.01); *C07K 14/70571* (2013.01); *A61K 38/00* (2013.01); *Y10S 514/909* (2013.01); *Y10S 514/91* (2013.01)

(58) Field of Classification Search
None
See application file for complete search history.

(56) References Cited

U.S. PATENT DOCUMENTS 5,990,159 A     11/1999   Meulemans et al.
8,436,021 B2 *   5/2013   Compan
2006/0116341 A1 *  6/2006   Compan

FOREIGN PATENT DOCUMENTS

| WO | 94/09828 | 5/1994 |
|---|---|---|
| WO | 94/14957 | 7/1994 |
| WO | 00/64441 | 11/2000 |
| WO | 00/77199 | 12/2000 |
| WO | 02/06272 | 1/2002 |

OTHER PUBLICATIONS

Ilse Van den Wyngaert et al., "Cloning and Expression of a Human Serotonin 5-HT$_4$ Receptor cDNA", Journal of Neurochemistry, vol. 69, No. 5, 1997, pp. 1810-1819.
Yuji Wada et al., "Action of the Selective 5-HT$_4$ Receptor Antagonist SB 204070A in the Rat Kindling Model of Epilepsy", Neuroscience Research Communications (1999), vol. 25(1), pp. 43-49.
Lance R. McMahon, Ph.D., "Antagonism of 5-Hydroxytryptamine$_4$ Receptors Attenuates Hyperactivity Induced by Cocaine: Putatige Role for 5-Hydroxytryptamine$_4$ Receptors in the Nucleus Accubens Shell", The Journal of Pharmacology and Experimental Therapeutics (1999), 291(1), pp. 300-3707.
Eckhard Bender et al., "Structure of the Human Serotonin 5-HT$_4$ Receptor Gene and Cloning of a Novel 5-HT$_4$ Splice Varian", Journal of Neurochemistry, New York, NY, US, vol. 74, No. 2, Feb. 2000, pp. 478-489.
Terry et al, Psychopharmacology, 135:407-415, 1998.
Marchetti et al, Neuropharmacology, 39:2017-2027, 2000.
Degen et al, Aliment Pharmacol Ther, 15:1745-1751, 2001.
Muller-Lissner et al, Aliment Pharmacol Ther, 15:1655-1666, 2001.
Klein, Obesity Research, 9:354S-358S, 2001.
Inui, FASED Journal, 14:2158-2170, 2000.
Metz et al, Pharmacology, Biochemistry and Behavior, Jun. 8, 2006, epub ahead of print.
Bockaert et al. Current Drug Targets—CNS and Neurological Disorders, 3:39-51, 2004.
Crowell et al, American Journal of Gastroenterology, 89:387-391, 1994.
Burns et al, Society for Neuroscience Abstracts, 26:991, Abstract 370.10, 2000.
Hegde et al., FASEB, 1996, vol. 10, pp. 1398-1407.
Dorland, "Anorexia", Dorland's Pocket Medical Dictionary, 1995, 25$^{th}$ Edition, p. 46.

(Continued)

*Primary Examiner* — Savitha Rao
*Assistant Examiner* — Gregg Polansky
(74) *Attorney, Agent, or Firm* — Oblon, McClelland, Maier & Neustadt, L.L.P.

(57) ABSTRACT

This invention relates to the use of a ligand of the 5-HT$_4$ receptor or of a pharmaceutically acceptable salt of this ligand and to a nucleic acid coding for a 5-HT$_4$ receptor or of a functionally equivalent receptor for a drug for treating and/or preventing a pathology associated with an obsessional behavior such as anorexia, bulimia and the addiction to drugs of abuse or obesity. The invention also relates to a method for identifying a compound that is biologically active in the treatment and/or the prevention of a pathology associated with an obsessional conduct or obesity including: a) placing the 5-HT$_4$ receptor or a functionally equivalent receptor in contact with this biologically active compound, and b) the determination of whether this biologically active compound is capable of modulating the basal activity of the 5-HT$_4$ receptor or of a functionally equivalent receptor.

6 Claims, 13 Drawing Sheets

(56) References Cited

OTHER PUBLICATIONS

Asakawa et al, Journal of Diabetes and its Complications, 20: 56-58, 2006.
Samanin et al, Neunyn-Schmiedeberg's Arch Pharmacol, 308: 159-163, 1979.
Hannon et al, Acta Biologica Szegediensis, 46(1-2): 1-12, 2002.
Guillaume Lucas, et al., "Serotonin$_4$ (5-HT$_4$) Receptor Agonists are Putative Antidepressants with a Rapid Onset of Action", Neuron 55, pp. 712-725, Sep. 6, 2007.
Beatriz A. Rocha, et al., "Increased vulnerability to cocaine in mice lacking the serotonin-1B receptor", Nature, vol. 393, May 14, 1998, pp. 175-178.
Terry Kenakin, "Collateral efficacy in new drug discovery", Trends in Pharmacological Sciences, vol. 28, No. 8, pp. 359-361, Jul. (2007).
Nathalie Castanon, et al., "Modulation of the effects of cocaine by 5-HT1B receptors: a comparison of knockouts and antagonists", Pharmacology, Biochemistry and Behavior, 67, 2000), pp. 559-566.
Shirley W. Tsang, et al., "A serotoninergic basis for hyperphagic eating changes in Alzheimer's disease", Journal of the Neurological Sciences, 288 (2010), pp. 151-155.
Paul L.R. Andrews, et al., "Signals for nausea and emesis: Implications for models of upper gastrointestinal diseases", Auton Neurosci., Apr. 30, 2006, 125(1-2): 100-115.doi:10.1016/j.autneu.2006.01.008.
Walter Kaye, et al., "Neurobiology of Anorexia and Bulimia Nervosa Purdue Ingestive Behavior Research Center Symposium Influences of Eating and Body Weight of the Lifespan: Children and Adolescents", Physiol Behav. Apr. 22, 2008; 94(1): 121-135. doi:10.1016/j.physbeh.2007.11.037.
WEBSTER'S II New Riverside University Dictionary, 1994, Houghton Mifflin Co., pp. 111.
Gregory Conductier, et al., "Adaptive Changes in Serotinin Neurons of the Raphe Nuciei in 5-HT$_4$Receptor Knock-Out Mouse", European Journal of Neuroscience, vol. 24, pp. 1053-1062, 2006.
James D. Moffatt, et al. "Role of the Epithelium and Acetylcholine in Mediating the Contraction to 5-Hydroxytryptamine in the Mouse isolated Trachea", British Journal of Pharmacology (2004), 141, pp. 1159-1166.
L.J. Dupont, et al., "The Effects of 5-HT on Cholinergic Contraction in Human Airways in vitro", Eur. Respir . J., 1999, 14:642-649.
"Loss of Appetite", American Cancer Society, 2009, downloaded from http://www.cancer.org/docroot/MIT/content/MIT_2_4X_Loss_of_Appetite.aspon_12/16/09, pp. 1-2 of 2.

* cited by examiner

FIG. 1

(1) molecular biology sector : preparation of DNA

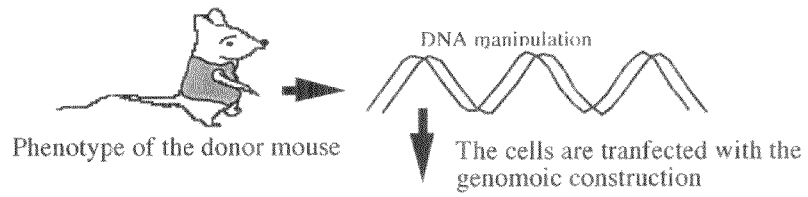

Phenotype of the donor mouse — The cells are tranfected with the genomoic construction (2) cellular culture sector : manipulation of the embryonic stem cells (ES)

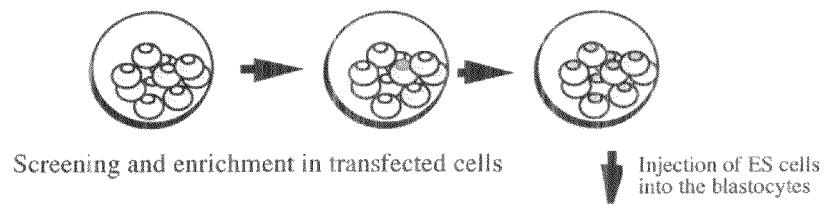

Screening and enrichment in transfected cells — Injection of ES cells into the blastocytes (3) sector associated with surgery : manipulation of the blastocytes

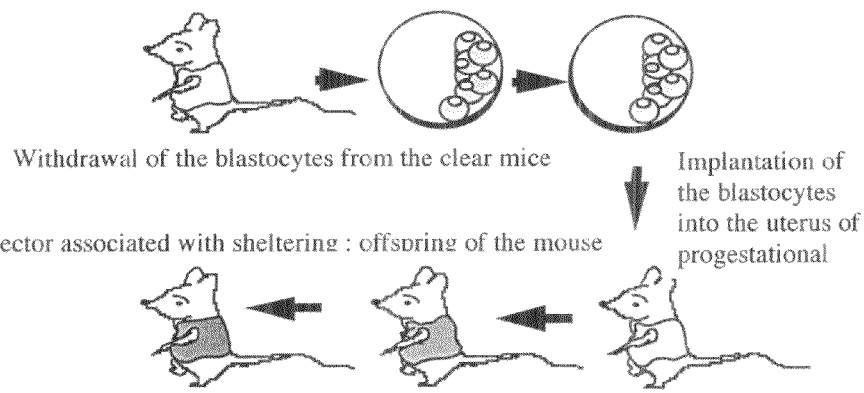

Withdrawal of the blastocytes from the clear mice — Implantation of the blastocytes into the uterus of progestational (4) sector associated with sheltering : offspring of the mouse

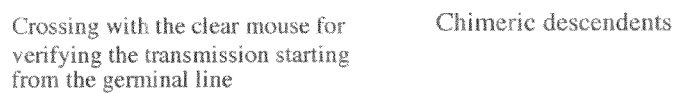

Crossing with the clear mouse for verifying the transmission starting from the germinal line — Chimeric descendents

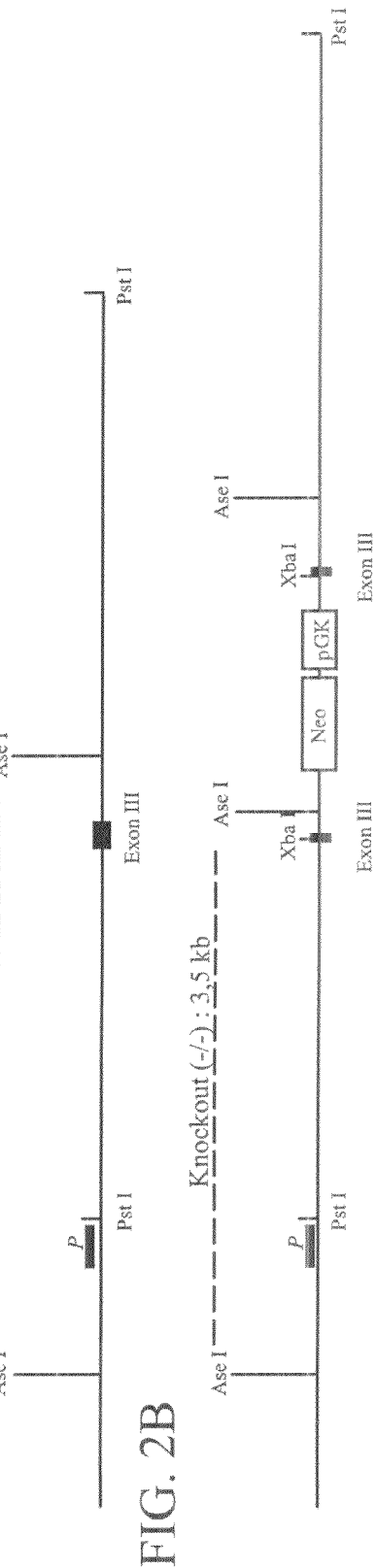
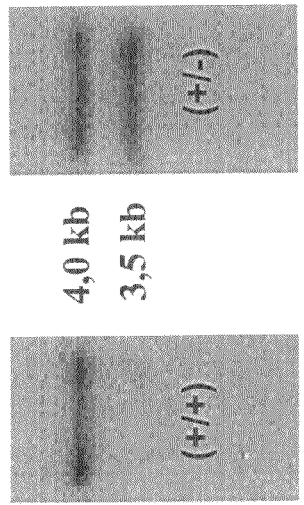
FIG. 2A
FIG. 2B
FIG. 2C

Taking of food after constraint test

Weight gain after constraint test

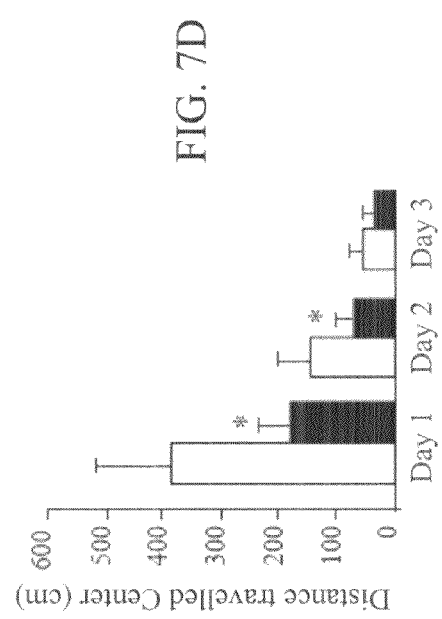
FIG. 7D
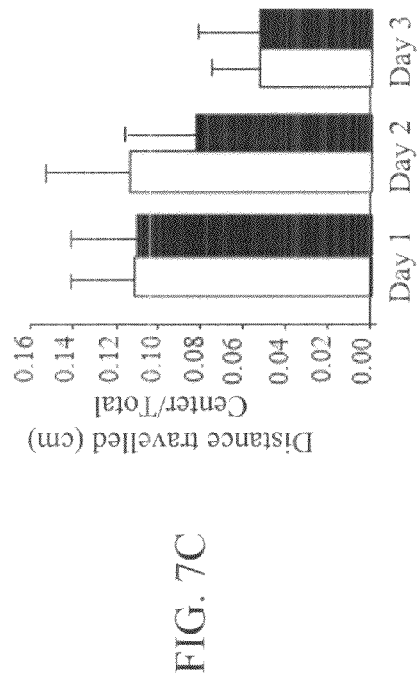
FIG. 7C
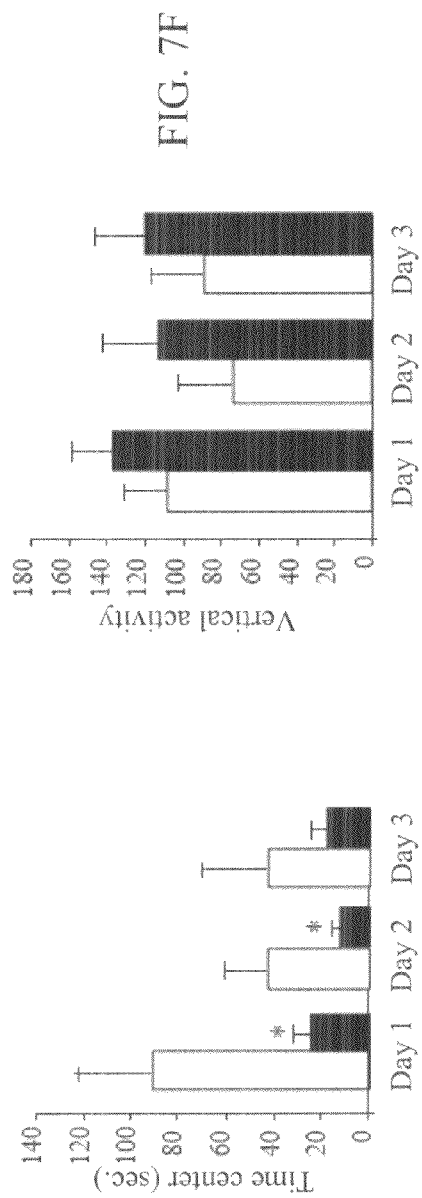
FIG. 7F
FIG. 7E

PHARMACEUTICAL COMPOSITION FOR TREATING AND/OR PREVENTING A PATHOLOGY ASSOCIATED WITH AN OBSESSIONAL BEHAVIOR OR WITH OBESITY

RELATED APPLICATION

This is a continuation of U.S. application Ser. No. 12/256,642 filed Oct. 23, 2008, now U.S. Pat. No. 8,436,021, which is a divisional of U.S. application Ser. No. 11/118,745 filed Apr. 29, 2005, pending, which is a continuation of International Application No. PCT/FR2003/003262, with an international filing date of Oct. 31, 2003 (WO 2004/042063, published May 21, 2004), and claims the benefit of French Patent Application No. 02/13725, filed Oct. 31, 2003.

FIELD OF THE INVENTION

This invention relates to the treatment and prevention of diseases associated with obsessional behaviors such as anorexia, bulimia and addiction to drugs of abuse, associated or not with stress as well as the treatment and prevention of obesity. The invention relates more particularly to a ligand of the $5\text{-HT}_4$ receptor for a drug for the treatment and/or prevention of diseases associated with obsessional behaviors and obesity.

BACKGROUND

Food problems coexist with anxiety and depression and represent an increasing concern of developed countries (Garrow, 1991; Kuczmarski et al., 1994). As for the majority of mental pathologies, the combination of the influence of environmental factors and a genetic predisposition seems to be responsible for these behavioral deficiencies (Fairburn et al., 1998; Lilenfeld et al., 1998; Barsh et al., 2000). The mothers of 75% of anorexic women suffer from depression or are alcoholics one year before the expression of the symptoms of their child. The anorexic syndrome is also detected more frequently in one and the same family than in the general population without any gene associated with this pathology having been identified. Bulimic behaviors, frequently concomitant with anorexia in the same individual, are characterized by impulsive and repeated phases of ingestion of an elevated amount of food.

Bulimia is thus classified among behaviors associated with addiction (international definitions of psychiatry, DSM). Food can be considered as a reward the obtention of which is based on will (wanting: appetite/incentive motivation) and is motivated by a component associated with hedonism (liking: pleasure/palatability) (Hoebel, 1997; Salamone et al., 1997; Stratford and Kelley, 1997; Stratford and Kelley, 1999). The excess or the absence of ingesting food is limited not only to metabolic and/or endocrinal deficiencies, but also depends on stress (Donohoe, 1984; Morley et al., 1983; Vergoni and Bertoline, 2000), on anxiety (Godart et al., 2000) and on depression (Viesselman and Roig, 1985; Casper, 1998).

The hypothalamus, the amygdala and the hippocampus are involved in the regulation of the consumption of food. Moreover, the activity of the neurons of the nucleus accumbens is modified during the anticipation or after the obtention of a classic reward such as food or drugs of abuse (Di Chiara, 1995; Hoebel, 1997; Koob and Nestler, 1997; Salamone et al., 1997).

Even though the emergence of discoveries shows the involvement of numerous peptides in the regulation of food behaviors (leptine, orexines, hypocretines, CART, NPY, POMC, CRH, TRH), the influence of classic neuromediators such as serotonin (5-HT) and dopamine (DA) cannot be avoided. GABA and glutamate should also be considered (Taber and Fibiger, 1997; Kelley and Swanson, 1997; Stratford and Kelley, 1997; Stratford et al., 1998).

Dopaminergic systems of the nucleus accumbens are involved in the anticipation of a reward (drugs of abuse, food). A chronic administration of clozapine, antagonist of the receptors of DA, induces a hyperphagia (Ackerman and Nolan, 1998; Allison et al., 1999). Cocaine and amphetamine, known for increasing the transmission of DA, are anorexigenic (Foltin and Evans, 1999).

Nevertheless, the serotoninergic systems remain an inevitable link that controls ingestion of food (Barnes and Sharp, 1999) due to the use of fenfluramine, inhibitor of the capture of serotonin in obese patients (Guy—B. Grand, 1995).

In sum, deficiencies of the combinations of interactions between factors of the environment (stress) and genetic factors (genes coding for receptors present in the brain) appear to be responsible for behavioral problems such as bulimia, anorexia or the addiction to drugs of abuse. These pathologies and, in a more evident manner, bulimia are considered today to be an addictive behavior.

On the neurobiological level, the state of our knowledge favors the combined intervention of several neuronal systems for regulating food behavior. The best known are the serotoninergic systems that express the cerebral messenger (neuromediator), that is 5-HT. The cerebral areas where their actions are manifested are primarily the hypothalamus, the amygdala and the nucleus accumbens.

The exact relationship between the effects of stress and 5-HT is rendered complex by the reciprocal influence between activities of the serotoninergic systems and the hypothalamo-pituitary axis (F. Chaouloff, 2000). On the other hand, application of stress brings about increases in the serotoninergic transmission.

Stress causes elevations in serotoninergic transmission. The experimental paradigms in which stresses associated with a conditioned fear bring about an increase in the metabolism and release of 5-HT in the median pre-frontal cortex (Adell et al., 1997; Inoue et al., 1994), the nucleus accumbens (Inoue et al., 1994; Ge et al., 1997), the amygdala (Amat et al., 1998) and the dorsal hippocampus (Ge et al., 1997; Joseph and Kennett, 1983). In particular, the stress of constraint (forced immobilization) increases renewal of 5-HT in the hypothalamus and the amygdala of the rat and mouse (Konstandi et al., 2000). In the same manner, the action of corticotropin-releasing hormone or factor (CRF) on the serotoninergic neurons of the corticomesolimbic system might be able to modify the rates of 5-HT (Lowry et al., 2000; Price and Lucki, 2001). In addition, alterations of the functioning of the receptors of the glucocorticoids produce variations in the concentration of 5-HT in the nucleus accumbens (Sillaber et al., 1998). Moreover, the repeated injection of corticosterone increases the activation of the neurons of the hippocampus (CA1) induced by an agonist of the $5\text{-HT}_4$ receptor (Zahorodna et al., 2000). Finally, numerous studies suppose that CRF is responsible for the anorexigenic effect of stress. In particular, the intracerebroventricular injection of CRF induces a diminution of ingestion of food in the mouse (Momose et al., 1999).

Serotonin inhibits ingestion of food. The pharmacological approaches combined with the strategies of transgenesis indicate that the receptors $5\text{-HT}_{1A/1B}$ and $5\text{-HT}_{2A/2C}$ are involved in regulating ingestion of food and, moreover, of stress (Bonasera and Tecot, 2000; Bouwknecht et al., 2001; Dourish et al., 1986; Heisler et al., 1998; Lucas et al., 1998; Samanin and Garattini, 1996). Anorexia associated with stress is assumed to result from the increase in the activity of serotoninergic neurons. Numerous studies attribute the anorexigenic effect of fenfluramine to the activation of the 5-HT$_{1B}$ receptor whereas that of the 5-HT$_{1A}$ (autoreceptor), inhibiting the release of 5-HT, induces an elevation of ingestion of food. The insensitivity of mice lacking receptor 5-HT$_{1B}$ in the injection of fenfluramine confirms its involvement in regulating ingestion of food (Lucas et al., 1998). The receptors 5-HT$_{2C}$ also intervene in the consumption of food because the mice deprived of it are obese (Heisler et al., 1998). Leptine is known to reduce ingestion of food, but it is not associated with this obesity (Nonogaki et al., 1998).

A recent study shows that the 5-HT$_{2C}$ receptors are also responsible for the anorexigenic effect of fenfluramine (Vickers et al., 2001). Finally, administration of tropisetrone, antagonist of the receptors 5-HT$_3$ and 5-HT$_4$, increase ingestion of food of a diet modified by a single amino acid (Erecius et al., 1996). However, this effect has been attributed to the 5-HT$_3$ receptor (Jiang and Gietzen, 1994). Consequently, no data is currently available concerning the contribution of the receptor 5-HT$_4$ in ingestion of food.

In sum, the current hypothesis for explaining that stress reduces ingestion of food is based on two series of parallel studies. The first one describes that stress increases the activity of the hypothalamo-pituitary axis (stress axis) and the serotoninergic neurons. Furthermore, hyperactivity of the hypothalamo-pituitary axis causes an increase in the rates of hormones such as CRF, urocortin and, in the final stage, of corticosterone. The second series of analyses shows that the hormones of the stress axis and 5-HT inhibit the taking of food.

As a consequence, numerous people propose the following sequence of events:

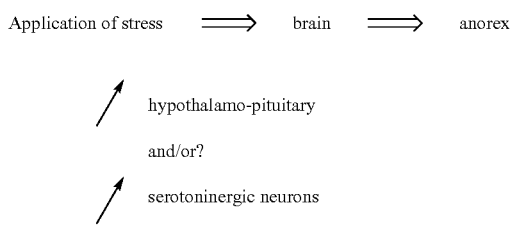

The set of the receptors of 5-HT are coupled with the G proteins with the exception of the receptor 5-HT$_3$, that is an ionic channel (Saudou and Hen, 1994). The receptors 5-HT$_{1A}$, 5-HT$_{1B}$, 5-HT$_{1D}$, 5-HT$_{1E}$ and 5-HT$_{1F}$ are negatively coupled to adenylate cyclase and have a strong affinity for 5-HT. Activation of receptors 5-HT$_2$ stimulates activity of phospholipase C (5-HT$_{2A/2C}$). The other receptors of 5-HT are positively coupled to adenylate cyclase and include 5-HT$_4$, 5-HT$_{drol}$ in the vinegar fly, and the receptors 5-HT$_6$ and 5-HT$_7$ in mammals. The receptor 5-HT$_4$ was described for the first time in the colliculi (Dumuis et al., 1988) and its stimulation brings about an elevation of the rates of AMPc in the hippocampus, the cerebral cortex, the atrium and the esophagus. In humans, nine subtypes of 5-HT$_4$ receptors named 5-HT$_{4A}$, 5-HT$_{4B}$, 5-HT$_{4C}$, 5-HT$_{4D}$, 5-HT$_{4E}$, 5-HT$_{4F}$, 5-HT$_{4G}$, 5-HT$_{4B}$ and 5-HT$_{4N}$ differ by their C-terminal end point (Bockaert et al., 2003, in the press, for review). The system for the transduction of receptors 5-HT$_{5A}$ is positively associated with adenylate cyclase. That of 5-HT$_{5B}$ has not yet been identified.

Functional influences of the 5-HT$_4$ receptors have been studied intensively in the gastrointestinal tract, but little data is available about their contributions in the brain. Of the set of the structures of the encephalon in rodents and in man, the greatest densities of the 5-HT$_4$ receptor are detected in the limbic system (Waeber et al., 1994). In particular, its concentration is three times greater in the shell than in the core of the nucleus accumbens (Compan et al., 1996). In the brain of rodents their rate varies during development and does not attain their adult level until the 21$^{st}$ day after birth (Waeber et al., 1994). In the encephalon of the rat the rates of mRNA's coding for the 5-HT$_4$ receptor are greatest in the olfactory system, the striatum, the nucleus accumbens, the habenula and the hippocampus (Gerald et al., 1995; Ulmer et al., 1996; Vilaro et al., 1996).

The agonists of 5-HT$_4$ receptors cause a reduction in the deficiencies of memorization and improve learning by setting transmission of acetylcholine in motion (J. Bockaert et al., 1998). It is tempting to suppose that the 5-HT$_4$ receptor can participate in the neuronal mechanisms of the nucleus accumbens associated with the learning of food. Four pharmacological studies have demonstrated a low contribution of the 5-HT$_4$ receptor in the "anxiety" state of the rat and of the mouse (Cheng et al., 1994; Silvesre et al., 1996; Kennett et al., 1997; Costall and Naylor, 1997). Inhibition of the 5-HT$_4$ receptor brings about a decrease in locomotive activity in the rat under basal conditions (Fontana et al., 1997), in the young mouse 20 to 27 days old (Semenova and Ticku, 1992) and can attenuate cocaine-induced hyperlocomotion (McMahon and Cunningham, 1999).

In the striatum, serotoninergic control of the rates of extracellular DA by the activation of the 5-HT$_4$ receptor is simultaneously described as exciting or inhibiting (Bonhomme et al., 1995; Steward et al., 1996; Deurwaërdere et al., 1997).

Finally, stimulation of the 5-HT$_4$ receptor brings about a closing of the ionic channels of potassium (Bockaert ea, 1998), which is capable of maintaining the excitability of neurons and augmenting the release of neuromediators. In agreement with this data, stimulation of the 5-HT$_4$ receptors leads to an increase in the rates of extracellular 5-HT in the hippocampus.

In sum, at the neurobiological level, 5-HT$_4$ receptors are known to intervene in learning and memory. The possible contribution in motor behavior and the anxiety state is currently described as moderate and has been little studied. A single study indicates that this receptor can intervene in the effect of cocaine on locomotive activity.

Furthermore, WO 97/29739 discloses use of antagonists of the 5-HT$_4$ receptor for preparation of a drug intended to avoid, alleviate, suppress or master the gastrointestinal effects caused by a selective inhibitor of the re-assimilation of serotonin.

WO 02/11766 discloses use of antagonists of the 5-HT$_4$ receptor in the prophylaxis or treatment of certain cardiovascular conditions.

SUMMARY OF THE INVENTION

This invention relates to a method of treating and/or preventing a pathology associated with an obsessional behavior and/or obesity including administering a therapeutically effective amount of a ligand of the 5-HT$_4$ receptor or of a pharmaceutically acceptable salt of this ligand to a mammal.

This invention also relates to a method of treating and/or preventing a pathology associated with an obsessional behavior and/or obesity including administering a therapeutically effective amount of a nucleic acid coding for a functional 5-HT$_4$ receptor or a functionally equivalent receptor to a mammal.

This invention further relates to a method of identifying a biologically active compound that can be used in a treatment and/or prevention of a pathology associated with an obsessional behavior and/or obesity including a) contacting a 5-HT$_4$ receptor or a functionally equivalent receptor contacting the biologically active compound, and b) determining whether the biologically active compound is capable of modulating basal activity of the 5-HT$_4$ receptor or of a functionally equivalent receptor.

BRIEF DESCRIPTION OF THE DRAWINGS

Other advantages and characteristics of the invention will appear from the following examples concerning the comparative study of mice disabled for the gene coding for the 5-HT$_4$ receptor of serotonin and of wild mice and in which reference is made to the attached drawings in which:

FIG. 1 is a schematic representation of objectives of the technical arts put in place to obtain transgenic mice.

FIG. 2 represents the disabling of the gene coding for the 5-HT$_4$ receptor of serotonin. FIG. 2A is a schematic representation of the dDNA fragment (6.5 kb) coding for transmembrane domains II and III of the 5-HT$_4$ receptor of serotonin (exon III). The dDNA sequence (P) represents the external probe for hybridizing a fragment of dDNA Ase I of 4 kb in wild mice. FIG. 2B is a schematic representation of the cloning vector. The expression of the gene coding for neomycine phosphotransferase (Neo) is under the control of a promoter (phosphoglyderate kinase I promoter: pGK). It was inserted into an enzymatic restriction site Xba in the dDNA sequence coding for the transmembrane domain III of the 5-HT$_4$ receptor. The size of the fragment of dDNA Ase I that can then be hybridized by the external probe is 3.5 kb and allows the identification of the mutated DNA. FIG. 2C is a Southern blot of the genomic DNA, of embryonic stem cells, previously digested by using the enzyme AseI and hybridized by the external probe (P).

FIG. 4 shows that the mice disabled for the gene coding for the 5-HT$_4$ receptor of serotonin show abnormal reactions for the taking of food and for weight gain after the stress of constraint or a forced immobilization.

This anorexigenic capacity is less efficacious in the mice lacking the 5-HT$_4$ receptor (FIG. 4b).

DETAILED DESCRIPTION

Figure 3:
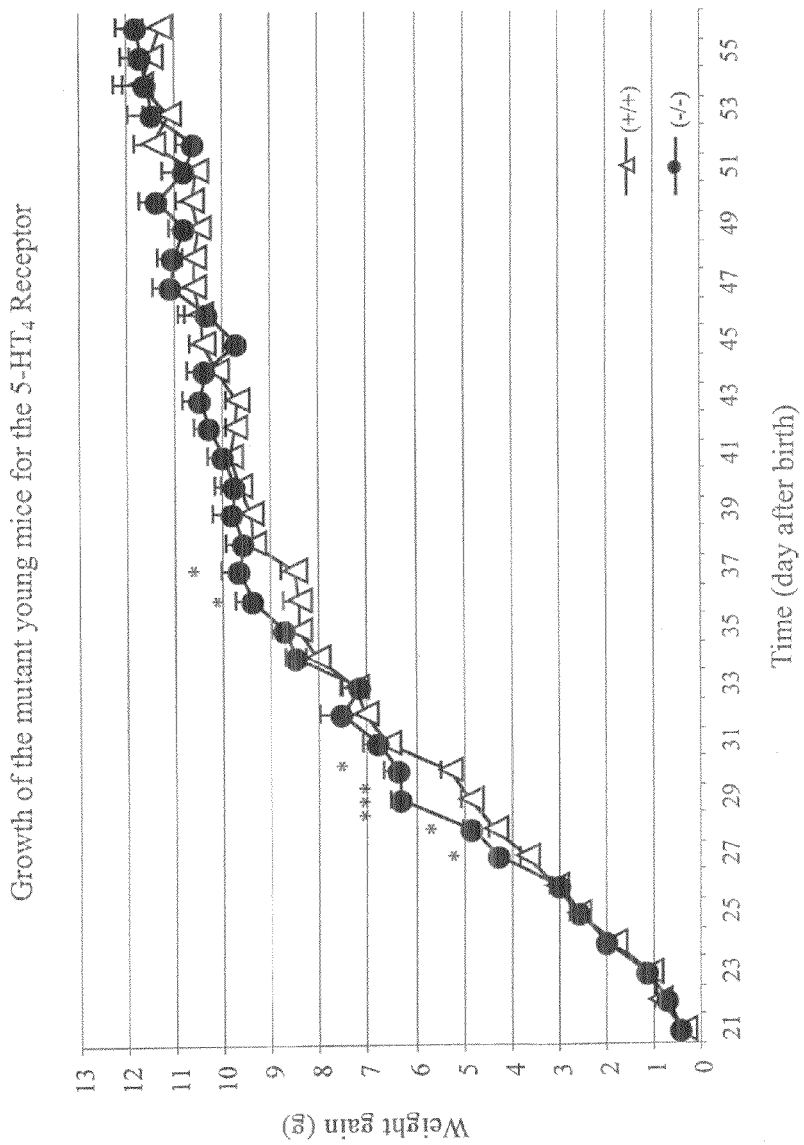
FIG. 3 shows that the mice disabled for the gene coding for the 5-HT$_4$ receptor of serotonin present a slightly increased weight gain during a short period of their development. The weight gain is the difference between the weights measured on a given day of the development (21 to 56) and that of the 20th day after birth. The data are the means±standard deviation from the average of the variations in the weight gain expressed in g. per day. The rate is measured starting from groups constituted by an average number of 21 wild ones (+/+) and 15 mutants (−/−) for each day born in one year between the 20th day preceding weaning and the 56th day of the acquisition of their fertility after their birth. Statistical analysis indicated that the weight gains of the mutant mice were significantly higher than those of the wild animals only on the days: 27 (+16%, $F_{1,72}$=6,54; n=40+/+, n=34−/−), 28 (+12%, $F_{1,67}$=4, 73: n=42+/+, n=27−/−), 29 (+30%, $F_{1,72}$=6, 54; n=23+/+, n=18−/−), 30 (+21%, $F_{1,72}$=6, 54; n=20+/+, n=19−/−), 36 (+12%, $F_{1,40}$=4, 06; n=22+/+, n=20−/−) and 37 (+13%, $F_{1,40}$=6, 18; n=25+/+, n=17−/−). No significant difference was detected between the two genotypes for the other days. The significant differences between the genotypes are marked by * $p<0.05$, *** $p<0.001$.

I have surprisingly discovered that the absence of the gene coding for the 5-HT$_4$ receptor of serotonin renders adult mice less sensitive to anorexigenic stress than wild animals from the embryonic period. In other words, certain stresses diminish ingestion of food in wild mice, but are less efficacious in mice lacking of the 5-HT$_4$ receptor. In the absence of this receptor, mice thus consume more food than non-genetically modified congeners.

Since stress contributes to the appearance of anorexia, accompanies bulimia and raises sensitivity to drugs of abuse, I discovered that the ligands of the 5-HT$_4$ receptor can attenuate manifestation of these pathologies (anorexia, bulimia, addiction to drugs of abuse associated or not with stress).

The term "5-HT$_4$ receptor" hereinafter denotes any one of the subtypes (or splicing variants) of the 5-HT$_4$ receptor such as, for example, the receptors 5-HT$_{4A}$, 5-HT$_{4B}$, 5-HT$_{4C}$, 5-HT$_{4D}$, 5-HT$_{4E}$, 5-HT$_{4F}$, 5-HT$_{4G}$, 5-HT$_{4H}$ and 5-HT$_{4N}$.

The invention therefore relates to the use of a ligand of the 5-HT$_4$ receptor or of a pharmaceutically acceptable salt of this ligand for a drug for treating and/or preventing a pathology associated with an obsessional behavior and/or obesity.

The term "a pathology associated with an obsessional behavior" hereinafter denotes the pathologies involving food problems and, in particular, anorexia, bulimia and addiction to drugs of abuse associated or not with stress.

The ligand of the 5-HT$_4$ receptor used in the framework of the invention for a drug for treating and/or preventing a pathology associated with an obsessional behavior and/or obesity is preferably not a ligand of the 5-HT$_3$ receptor and is a specific ligand of the 5-HT$_4$ receptor.

Inasmuch as I have demonstrated that the 5-HT$_4$ receptor is involved in the anorexigenic effective stress, it is now possible to use an agonist of this receptor in a drug intended to treat and/or prevent bulimia whereas an antagonist or also an inverse agonist of this receptor can be used for a drug intended to treat and/or prevent pathologies associated with an obsessional behavior selected from the group constituted by anorexia and addiction to drugs of abuse.

The following terms hereinafter have the following meanings:

Agonist: Any molecule capable of engendering by its linkage to its receptors a biological response similar to an endogenic mediator.

Antagonist: Any molecule capable of inhibiting the action of agonists.

Inverse agonist: Any molecule capable of inhibiting the intrinsic (or basal) activity of the receptor.

All the agonists, all the inverse agonists and all the antagonists, whether known or not yet identified, specific to the 5-HT$_4$ receptor may be used in this invention.

Bockaert et al. (1997) described the chemical structure of agonists and of antagonists of the 5-HT$_4$ receptor. The agonists described belong to 6 chemical classes that are the indoles, the benzamides, benzoate, the aryl cetones, the benzimidazolones and the 1,8-naphthalimides. The antagonists described belong to 5 chemical classes that are the carboxylates of indole, imidazolpydridine, the benzoates, the aryl cetones, the benzimidazolones and the 1,8 naphthalimides. These agonists and antagonists can be used in accordance with aspects of this invention. The inverse agonists described in Claeysen et al., (2001) and in Joubert et al. (2002) can also be used in accordance with aspects of this invention.

Moreover, WO 97/29739, WO 02/11766 and WO 02/36113, respectively, disclose antagonists and agonists of the 5-HT$_4$ receptor, that can also be used in accordance with aspects of this invention.

The agonists that can be used herein are selected from the group comprising metoclopramide, HTF919 (3-(5-methoxy1H-indole-3-ylmethylene)-N-pentylcarbazimidamide hydrogen maleate), LS650155, BRL 20627, BRL 24682, BRL 24924, cisapride (Carlsson et al., 1997), ML 1035 (4-amino-5-chloro-2-[2-(methylsulfinyl)-ethoxy]-N-[(diethylamino)ethyl]benzamide hydrochloride), mosapride (Carlsson et al., 1997), R076186, renzapride, RS 67506 (1-(4-amino-5-chloro-2-methoxyphenyl)-3-[1-(2-methyl sulphonylamino)ethyl-4-piperidinyl]-1-propanone hydrochloride), cinitapride, SB 205149, SC 49518 (N-[exo-(hexahydro-1H-pyrrolizine-1-yl)methyl]-2-methoxy-4-amino-5-chlorobenzamide HCl), SC 52491, SC53116 (4-amino-5-chloro-N-[(hexahydro-1H-pyrrolizin-1-yl)methyl]2-methoxybenzamide), SDZ 216454, TKS 159 (4-amino-5-chloro-2-methoxy-N-[(2S,4S)-1-ethyl-2-hydroxymethyl-4-pyrrolidinyl]benzamide, Y 34959, YM 09151 (N-(1-benzyl-2-methylpyrrolidine-3-yl)-5-chloro-2-methoxy-4-methylaminobenzamide, YM 47813, zacopride (4-amino-5-chloro-2-methoxy-N-(1-azabicyclo[2.2.2]oct-3-yl)benzamide), ML 10302 (2-piperidinoethyl 4-amino-5-chloro-2-methoxybenzoate), RS 57639, SR 49768 (2-[(3S)-3-hydroxypiperidino]ethyl-4-amino-5-chloro-2-methoxybenzoate), ADR 932, prucalopride (R093877; 4-amino-5-chloro-2,3-dihydro-N-[1-(3-methoxy propyl)-4-piperidinyl]-7-benzofurancarboxamide monohydrochloride), SK 951, RS67333 (1-(4-amino-5-cloro-2-methoxyphenyl)-3-(1-n-butyl-4-piperidinyl)-1-propanone), RS 17017, RS 56532, YM 53389, BIMU1 (3-ethyl-2,3-dihydro-N-[endo-8-methyl-8-azabicyclo(3.2.1)oct-3-yl]-2-oxo-1H-[benzimidazole-1-carboxamide), BIMU8 (endo-N-8-methyl-8-azabicyclo[3.2.1]oct-3-yl)-2,3-dehydro-2-oxo-3-(prop-2-yl)-1H-benzimid-azole-1-carboxamide), DAU 6215 (3-alpha-tropanyl 1H-benzimidazolone-3-carboxamide chloride), DAU 6236, 5-methoxytryptamine, 2-methylserotonin and 5-hydroxy-N,N-di-methyltryptamine and 5-carboxamidotryptamine.

The antagonists that can be used are advantageously selected from the group comprising tropisetron (ICS 205 930; [(3a tropanyl)-1H-indole-3-carboxylic acid ester]), RS 100235 (1-(8-amino-7-chloro-1,4-benzodioxan-5-yl)-3-[[3,4-dimethoxyphenyl) prop-1-yl]piperidine-4-yl]propan-1-one, RS 39606, A-85380 (3-(2(S)-azetidinylmethoxy)pyridine), GR 113808 (1-[2-(methylsulphonyl)amino]ethyl]-4-piperidinyl]methyl 1-methyl-1H-indole-3-carboxylate), GR 125487 (1-[2-(methylsulphonyl)amino]ethyl]-4-piperidinyl] methyl-5-fluoro-2-methoxy-1H-indole-3-carboxylate), GR 138897 ([1-[2-[methylsulphonyl)amino]-4-piperidinyl]methyl[2-(3-methyl-1,2,4-oxadiazon-5-yl)phenyl]carbamate), SB 203186(1-piperidinyl)ethyl 1H-indole 3-carboxylate), SDZ 205-557 2-methyox-4-amino-5-chlorobenzoic acid 2-(diethylamino)ethyl ester hydrochloride, LY 353433 (1,(1-methylethyl)-N-(2-(4-(((tricyclo[2-(3.3.1.1$^{3,7}$]dec-1-yl-carbonyl)amino-1-piperidinyl)ethyl)-1H-indazole-3-carboxamide), LY 297582, RS 23597 (3-piperidine-1-yl)propyl-4-amino-5-chloro-2-methoxybenzoate hydrochloride, SB 204070 (1-butyl-4-piperidinyl)methyl 8-amino-7-chloro1,4-benzodioxan-5-carboxylate), DAU 6285 ((endo-6-methoxy-8-methyl-8-azabicyclo[3.2.1]oct 3-yl)-2,3-dihydro-2-oxo-1H-benzimidazole-1 carboxylate hydrochloride), SC53606 (1-S,8-S)—N-[hexahydro-1H-pyrrolizin-1-yl)methyl]-6-chloroimidazo[1,2-a]pyridine-8-carboxamide hydrochloride), SC56184, RS67532 (1-(4-amino-5-chloro-2-(3,5-dimethoxy benzyloxyphenyl)-5-(1-piperidinyl)-1-pentanone), GR 125487 (1-[2(methylsulfonyl)amino[ ]ethyl]-4-piperidinyl]methyl-5-fluoro-2-methoxy-1H-indole-3-carboxylate hydrochloride), SB 207078, SB 207266 (N-[1-″butyl-4-piperidinyl)methyl]-3,4-dihydro-2H-[1,3] oxazino[3,2-adindole-10-carboxamide), RS 39604 (1-[4-amino-5-chloro-2-(3,5-dimethoxyphenyl)methyloxy]-3-[1 [2-methylsulphonylamino]ethyl]piperidine-4-yl]propan-1-one, RS 1003002 (N-2-(4-(3-(8-amino-7-chloro-2,3-dihydro-1,4-benzodioxin-5-yl)-3-oxopropyl) piperidin-1-yl) ethyl)-methanesulfonamide), ML 10375 (2-cis-3,5-dimethylpiperidino)ethyl 4-amino-5-chloro-2 methoxybenzoate), SB 207710 (1-butyl-4-piperidinyl)methyl-8-amino-7-1,4-benzodioxan-5-carboxylate), SB205800 (N-(1-butyl-4-piperidinyl)methyl-8-amino-7-chloro-1,4-benzodioxan-5-carboxamide), N 3389, FR 1052 and R 50595.

The inverse agonists that can be used herein are selected from the group comprising RO 116-2617, RO 116-0086 and RO 116-1148.

The amount of ligand of the 5-HT$_4$ receptor or of a pharmaceutically acceptable salt of this ligand that is effective in the treatment and/or prevention of a pathology associated with an obsessional behavior and/or obesity depends on the nature of the disorder and can be readily determined by known experimental techniques and clinical standards. Furthermore, simple in vitro trials can optionally be used to identify the ranges of optimal dosages. The effective dosages can be readily extrapolated from dosage-response curves obtained from the in vitro test systems or from the animal model.

The pharmaceutical compositions for treating and/or preventing a pathology associated with an obsessional behavior and/or obesity comprising a ligand of the 5-HT$_4$ receptor are prepared in accordance with standard pharmaceutical practices. These pharmaceutical compositions are presented in a form appropriate for a parenteral administration, oral, rectal, nasal, transdermic, pulmonary, central or systemic administration or the like.

The pharmaceutical compositions contain in addition to the ligand of the 5-HT$_4$ receptor or the pharmaceutically acceptable salt of this ligand at least one pharmaceutically acceptable vehicle selected as a function of the administration path and of the form of administration.

In another aspect, the invention relates to restitution in targeted areas of the brain of a "wild" 5-HT$_4$ receptor for treating or preventing pathologies associated with obsessional behaviors and/or obesity and, in particular, pathologies associated with obsessional behaviors with the hypothesis that these pathologies are caused by one or several mutations in the gene coding for the 5-HT$_4$ receptor.

Consequently, the invention relates to the use of a nucleic acid coding for a functional 5-HT$_4$ receptor or a functionally equivalent receptor for the preparation of a drug for treating and/or preventing a pathology associated with an obsessional behavior.

The term "functional 5-HT$_4$ receptor" hereinafter denotes a wild 5-HT$_4$ receptor present in normal pharmacological properties.

The term "functionally equivalent receptor" hereinafter denotes a receptor whose amino acid sequence is close to that of the 5-HT$_4$ receptor (at least 90% identical and preferably at least 95% identical) and is activated by the same agonists and with the same intensity as the wild 5-HT$_4$ receptor.

The molecule of nucleic acid coding for a functional 5-HT$_4$ receptor or a functionally equivalent receptor is advantageously a molecule coding for a mammalian 5-HT$_4$ receptor and, in particular, a molecule coding for a human 5-HT$_4$ receptor. These sequences can be obtained in Genbank under the numbers:

For the human: Y09586 (5-HT$_{4A}$), Y10437 (5-HT$_{4B}$), Y12506 (5-HT$_{4C}$), Y15507 (5-HT$_{4D}$), AJ011371 (5-HT$_{4G}$);

For the mouse: Y09587 (5-HT$_{4A}$), Y09585 (5-HT$_{4B}$), Y09588 (5-HT$_{4E}$), AJ011370 (5-HT$_{4F}$);

For the rat: U20906 (5-HT$_{4A}$), 020907 (5-HT$_{4B}$) and AJ011371 (5-HT$_{4E}$);

For the guinea pig: Y13585 (5-HT$_{4B}$).

As a result of degeneration of the genetic code, other nucleic acid sequences coding for substantially the same amino acids can be used in the invention. The sequences are by way of example and in a non-exhaustive manner nucleotide sequences comprising all or part of the nucleic acid coding for a 5-HT$_4$ receptor modified at the level of one or several codons in such a manner as to produce a silent mutation. The sequences of nucleic acid that can be used in the invention can be obtained by various methods known in the art, e.g., via cDNA obtained from the mRNA of the 5-HT$_4$ receptor after a reverse transcription.

In an advantageous manner the nucleus accumbens, the amygdale, the hippocampus and the hypothalamus or the cerebral structures in which the simultaneous restoration of the expression of the gene coding for the 5-HT$_4$ receptor and the removal of the deficiencies in the regulation of the taking of food associated with this absence are envisioned. Only a simultaneous restoration of the molecular and cellular deficiencies (rate of the endogenic monoamines, activity of the serotoninergic neurons, for example) and behavioral deficiencies as a consequence of the reestablishing the expression of this gene permit a validation of a causal connection between the molecular and behavioral phenotype.

To advantageously express a functional $5\text{-}HT_4$ receptor or a functionally equivalent receptor in the nucleus accumbens, the amygdale, the hippocampus and the hypothalamus the use of transfer vectors is possible such as non-viral or viral vectors containing nucleic acid molecules coding for a functional $5\text{-}HT_4$ receptor or a functionally equivalent receptor.

Among the viral vectors that can be used in the invention, viruses associated with the adenovirus of type 2, vectors stemming from the lentivirus with different pseudotypes, vectors stemming from viruses of feline immunodeficiency and vectors stemming from the foamy virus, among others, are possible. The viral vectors should be disencumbered of any pathogenic and/or toxic effect.

The expression of the molecule of nucleic acid coding for a functional $5\text{-}HT_4$ receptor or a functionally equivalent receptor contained in these vectors is advantageously placed under the control of adequate promoters as a function of the target tissue. For the expression of a functional $5\text{-}HT_4$ receptor or a functionally equivalent receptor in the nucleus accumbens, the amygdale, the hippocampus and/or the hypothalamus, an advantageously used promoter can be the promoter of the gene coding for the transporter for capturing dopamine for the nucleus accumbens.

The invention relates in another aspect to a method of identifying a biologically active compound that can be used in the treatment and/or prevention of a pathology associated with an obsessional behavior and/or obesity and in particular a biologically active compound for the treatment and/or prevention of a pathology associated with an obsessional behavior comprising the following steps:

a) placing the $5\text{-}HT_4$ receptor or a functionally equivalent receptor in contact with this biologically active compound, and b) determining whether this biologically active compound is capable of modulating the basal activity of the $5\text{-}HT_4$ receptor or of a functionally equivalent receptor.

The term "biologically active compound" hereinafter denotes any natural or synthetic chemical compound capable of attenuating the symptoms of a pathology associated with obsessional behaviors after its administration.

Stage (a) of the method can comprise the following steps:
i) placing cells in a culture that express a functional $5\text{-}HT_4$ receptor or a functional equipment receptor, and
ii) incubation of the cells with this biologically active compound.

The terms "functional $5\text{-}HT_4$ receptor" and "a functionally equivalent receptor" are previously defined.

The cells cultivated in stage (i) of the method are advantageously cells that overexpress a functional $5\text{-}HT_4$ receptor or a functionally equivalent receptor on their surface. Every cell capable of overexpressing a functional $5\text{-}HT_4$ receptor or a functionally equivalent receptor on its surface can be used herein. The human embryonic cells HEK 293 can be cited as examples and in a non-exhaustive manner.

A molecule of nucleic acid coding for a functional $5\text{-}HT_4$ receptor or a functionally equivalent receptor can be used to transform the cells that overexpress a functional $5\text{-}HT_4$ receptor or a functionally equivalent receptor.

The vector for transforming cells overexpressing a functional $5\text{-}HT_4$ receptor or a functionally equivalent receptor can comprise at least one molecule of nucleic acid coding for a functional $5\text{-}HT_4$ receptor or a functionally equivalent receptor like the one described above, advantageously associated with control sequences adapted to the process of the expression or of the production of these receptors in a cellular host. The vector used is selected as a function of the host (cultivated cells) in which it is to be transferred; this can be any vector such as a plasmid. Preparation of these vectors as well as production or expression of the receptor in a cellular host can be realized by techniques of molecular biology and of genetic engineering well-known in the art.

A compound capable of modulating the base activity of a receptor is either an agonist, an inverse agonist or an antagonist of this receptor. Linkage of an agonist, an inverse agonist or an antagonist to a receptor brings about changes in the conformation of this receptor and in the cell a transduction of the signal by the intermediation of second messengers is observed. Consequently, step (b) measures by any adapted means the affinity between the receptor and the biologically active compound after they have been brought into contact.

Modulation of the basal activity of the $5\text{-}HT_4$ receptor or of a functionally equivalent receptor can be advantageously measured via activation (for an agonist) or inhibition (for an antagonist or for an inverse antagonist) of the transduction of the signal from the $5\text{-}HT_4$ receptor. One skilled in the art, knowing the cascade of events induced during transduction of the signal from this receptor, is capable of determining adequate methods and conditions for measuring the activation or the inhibition of the transduction of the signal from the 5-HT.sub.4 receptor, e.g., by measuring the quantity of cAMP before and after the placing in contact with the functionally active compound.

In another aspect of the method stages (a) and (b) can be realized by fixing one or several $5\text{-}HT_4$ receptors or functionally equivalent receptors on one or several membranes. The $5\text{-}HT_4$ receptors or the functionally equivalent receptors can also be integrated into a biosensor. In such a system it is possible to visualize in real time the interactions between the compound to be tested and the receptor. One of the partners of the receptor/ligand couple is fixed on an interface that can contain a matrix covered with aliphatic chains. This hydrophobic matrix can be readily covered by a lipidic layer by the spontaneous fusion of liposomes injected at its contact. The $5\text{-}HT_4$ receptors or functionally equivalent receptors inserted in the liposomes can then be integrated into the biosensors. The biologically active compound is then analyzed relative to one or several $5\text{-}HT_4$ receptors or functionally equivalent receptors. In addition, the technology of the biosensor allows the affinity of the linkage to be measured.

The invention also relates to a method for treating and/or preventing a pathology associated with an obsessional behavior comprising administering an efficacious quantity of a ligand of $5\text{-}HT_4$ receptors such as previously defined or of a nucleic acid coding for a $5\text{-}HT_4$ receptor or functionally equivalent receptor such as previously defined.

The results obtained herein show that the $5\text{-}HT_4$ receptors control the leptine rates and can, by virtue of this fact, intervene in the control of obesity. In fact, I have shown that the absence of $5\text{-}HT_4$ receptors induces a reduction of the leptine rates. This involvement in obesity is possible because obesity has been observed in mutant mice deprived of the $5\text{-}HT_4$ receptor more than 6 months old and therefore older than those used in the experimental part below.

Consequently, this invention relates to the use of a ligand of the $5\text{-}HT_4$ receptor such as it was previously defined and in particular an agonist of the $5\text{-}HT_4$ receptor such as it was previously defined for a pharmaceutical composition for the treatment and/or prevention of obesity. All embodiments envisaged for the pharmaceutical compositions for the treatment and/or prevention of obsessional behaviors apply to the treatment and/or prevention of obesity.

In a particular aspect, the invention relates to the restitution in targeted areas of the brain of a "wild" 5-HT$_4$ receptor for treating or preventing obesity with the belief that this pathology is caused by one or several mutations in the gene coding for the 5-HT$_4$ receptor.

Consequently, the invention relates to the use of a nucleic acid coding for a functional 5-HT$_4$ receptor or a functionally equivalent receptor for a drug for treating and/or preventing obesity. The various embodiments envisaged above (mammalian 5-HT$_4$ receptor, human 5-HT$_4$ receptor, viral or non-viral transfer vector and the like) also apply to the treatment and the prevention of obesity.

Thus, the invention provides a method for the treatment and/or prevention of obesity comprising administering an efficacious quantity of a ligand and, in particular, an agonist of the 5-HT$_4$ receptors such as they are defined above or of the nucleic acid coding for a functional 5-HT$_4$ receptor or a functionally equivalent receptor such as defined above.

The invention relates to a method for identifying a biologically active compound capable of being used in the treatment and/or the prevention of obesity and, in particular, a biologically active compound for the treatment and/or the prevention of obesity comprising the following steps:

a) placing the 5-HT$_4$ receptor or a functionally equivalent receptor in contact with this biologically active compound, and b) determination of whether this biologically active compound is capable of modulating the basal activity of the 5-HT$_4$ receptor or of a functionally equivalent receptor.

Various aspects of the identification of a biologically active molecule in the treatment and/or the prevention of a disease associated with an obsessional behavior apply with such modifications as the circumstances require to the identification of a biologically active molecule in the treatment and/or the prevention of obesity. Taking into account the results obtained herein, it is evident to one skilled in the art that a molecule active in the treatment and/or the prevention of obesity should behave like an agonist of the 5-HT$_4$ receptor.

I. Materials and Methods

I.1. Generation of Mice Disabled for the Gene Coding for the 5-HT$_4$ Receptor of Serotonin a. Principle Transgenesis is a general principle and comprises modification of the expression of a gene of interest in a living organism. In the mouse these modifications require three successive steps (FIG. 1). The first step uses a large number of techniques of molecular biology. It consists of the obtention of a genomic construction resulting from deletion or insertion of the gene of interest or also from the modification by directed mutagenesis of several nitrogenous bases. The second step uses transfection of embryonic cells by transfection of the genomic construction in totipotent, murine embryonic cells ("embryonic stem cells" or ES). Insertion of the mutated gene into their genome is brought about by random homologous recombination in a stable manner. The recombinant clones are then selected by using an antibiotic (G418 or neomicine) because a resistance gene was previously inserted during the realization of the genomic construction. The last stage is the injection of the positive clones into the blastocytes (FIG. 2).

b. Verification of the Absence of the 5-HT$_4$ Receptors in the Mutant Mice

To verify the absence of the 5-HT$_4$ receptors in the mutant mice the technique of radiography was used as previously described (Compan et al., 1996) from cerebral sections of the wild animals, heterozygotes and mutants. The linkage sites of the 5-HT$_4$ receptor have been marked by a selective radioligand, the [$^3$H]GR113808 (Amersham), antagonist of the 5-HT$_4$ receptor.

In the wild mice a heterogeneous distribution of the linkage sites marked by the [$^3$H]GR113808 was observed in the base ganglia, the limbic system or the hippocampal formation has already observed for the rat ((Waeber et al., 1994, Compan et al., 1996). No specific marking was detected in the mutant mice. The density of the marked linkage sites was reduced in all the cerebral structures analyzed in the heterozygotous mice in comparison to the wild mice (Table 1).

TABLE 1

Density of the linkage sites of the 5-HT$_4$ receptor marked by the [$^3$H]GR113808 (0.1 nM) in adult mice of the wild and of the heterozygotous genotype.

| | $B_{max}$ (average ± standard deviation from the Average in fmol/mg of protein) | |
|---|---|---|
| Regions | Wild | Heterozygotous |
| Olfactory tubercles | 201 ± 34 | 66 ± 16 (67%) |
| Ventral pallidum | 171 ± 37 | 53 ± 21 (70%) |
| Nucleus accumbens | 116 ± 28 | 36 ± 16 (68%) |
| Rostral striatum | 115 ± 15 | 48 ± 11 (48%) |
| Caudal Striatum | 142 ± 25 | 18 ± 10 (85%) |
| Globus pallidus | 90 ± 20 | 14 ± 8 (85%) |
| Hippocampus | 104 ± 11 | 9 ± 8 (91%) |

* Considering a concentration of 1 mg of protein/10 mg of cerebral tissue.

The genotype of the previously identified was also verified by using the technique of polymerization in a chain reaction (touchdown protocol PCR). All the animals tested were born from heterozygotous couples and aged between 4 and 6 months. We obtained 18% of the mutant mice over a period of three years. We still do not have an explanation about the value of this report, which does not follow the Mendelian laws (Table 2).

TABLE 2

Mendelian relationships obtained after the crossing of heteozygotous mice

| Wild | Heterozygotous | Homozygotous |
|---|---|---|
| 36% (414) | 46% (632) | 18% (209) |

The mice deprived of the 5-HT$_4$ receptors develop without apparent problems with the exception of a weight gain that is significantly more elevated than that of the wild mice over a short period of their development (FIG. 3). No significant difference of weight was detected in the mice aged from 4 to 6 months (not illustrated). Since classic mechanisms of adaptation of the neuronal systems can occur during the course of development, the hypothesis according to which an unaccustomed context could induce problems in the consumption of food during their adult period was formed by the inventor.

I.2. Behavioral Tests

The consumption of food and weight gain of the mutant mice in comparison to the wild animals were therefore measured after the constraint test (forced immobilization) had been used, which is known for constituting an anorexigenic stress. In the same manner, ingestion of food was evaluated after the using of conflict tests: The superelevated cross labyrinth and the open field. In these two experimental tests the rodents were confronted with a conflict between the motivation to explore a new environment and the fear of open and/or superelevated spaces.

a. Animals

The wild and mutant animals stemmed from the line Sv 129/Ter (Phillips et al., 1999) and were born from crossings of heterozygotous mice (+/−) for the mutation of the gene coding for the $5\text{-}HT_4$ receptor to retain the same genetic predisposition between the two genotypes. The animals were raised and manipulated under conditions of standard illumination at the controlled and constant temperature and degrees of hydrometry of 22° C. and 55% relative humidity. A day/night cycle (12/12 h) was artificially maintained. The food was in the form of cylindrical croquettes (23% proteins; 3.5% raw fatty matter; 3% raw cellulose; 7.5% raw ash; 12% humidity). The genotype of the mice was identified by using the technique of polymerase chain reaction or PCF. All the experiments were performed with animals with an average age of 4 to 6 months.

a. Evaluation of Ingestion of Food

After the Constraint Test.

Each of the tests was divided into three phases: A period of habituation (7 days), the day of the constraint stress (immobilization for 110 min) and a recovery stage (10 days). The mice were divided into a control group and a constraint group. On the stress day the wild mice disabled for the gene coding for the $5\text{-}HT_4$ receptor received an injection of NaCl 9%, 1 mg/kg of RS 39604, antagonist of the $5\text{-}HT_4$ receptor. In parallel thereto, a group of mice did not receive any treatment and were weighed like the previous mice and immobilized, if necessary, 10 minutes after the start of their manipulation. Ingestion of food was then measured 2 h 30 min, 3 and 5 h and each day during the recovery period.

After an Isolation of 3 h (Procedure 1).

The animals are isolated in a cage in the presence of food and water ad libitum. The weight of the food and of the animal was evaluated before and 3 h after isolation. The difference between two successive weights revealed the quantity of food ingested by the mouse. As the bottom of the cage was a grill, it was possible to evaluate the quantity of food wasted by each animal.

After the Superelevated Cross Labyrinth (Procedure 2: Moderate Stress).

The same animals were regrouped four to a cage for one week in a residence chamber. On the test day, after a period of 30 min the animals were placed in the superelevated cross labyrinth and then isolated to evaluate their consumption of food 3 h after the beginning of the test.

After the Superelevated Cross Labyrinth Anticipated by an Incision (Procedure 3: High Stress).

During a period of habituation each mouse was isolated for four days (96 hours) in the presence of food and water supplied ad libitum. The weight of the mice and of the food consumed was measured daily at the same hour to establish a baseline. On the fourth day a small incision on the tail was made. A blood sample was then taken for 10 min to analyze the plasmatic rates of corticosterone before the injection and the conflict test. The superelevated cross labyrinth also represents a stress inductor because it induces an increase of the rates of corticosterone (Rodgers et al., 1999). Incisions were made in a different room of the test area and all useful precautions were taken to avoid any stress aside from the incision of the tail and the immobilization prior to this operation. The blood samples obtained were centrifuged 10 min at 10,000 rpm and the plasma then stored at −80° C. until the further dosages. The corticosterone was dosed using the technique of radioimmunoassay (ICN Clinisciences). Once the sample was concluded the animals were placed in the test area.

On the fifth day the animals received an intraperitoneal injection (i.p.) of NaCl at 9. The injections were made 10 min before the mice were placed in the superelevated cross labyrinth. The animals were divided into two test groups of wild mice treated with NaCl (n=8) and mutants that also received an injection of NaCl (n=12). The mice were placed in the center of the superelevated cross labyrinth 10 min after the injection. A small incision on the tail was again made 30 min after the test, in which the rates of corticosterone reached their maximum and remained elevated for four hours (Natelson et al., 1987). After the test, two successive evaluations of the taking of food were carried out 3 h after the start of the test.

After the Open Field.

We proceeded in the same manner as in the case of procedure 2 to evaluate ingestion of food 3 h after the beginning of the confrontation with the open field. Furthermore, motor activity of the mice was evaluated one month after procedures 2 and 3.

After the Administration of Drugs.

Each drug used to treat the wild mice disabled for the gene coding for the $5\text{-}HT_4$ receptor was diluted extemporaneously in a saline solution of NaCl (0.9%) and injected in a systemic manner (i.p.). The injection volume of each treatment was 200 μL for 30 g. The wild mice or those disabled for the $5\text{-}HT_4$ receptor (n=35) received the following treatments: NaCl, MDMA (or ecstasy or 3,4-N-methylene dioxymethamphetamine, SIGMA, 10 mg/kg), RS 39604, RS 102221/MDMA.

The MDMA (10 mg/kg, Sigma, user license 9900431 S, V. Compan) and RS 39604 (0.5 mg/kg), antagonist of the $5\text{-}HT_4$ receptor, were administered by themselves or in a combined treatment to the wild mice or those deprived of the $5\text{-}HT_4$ receptor (n=12-17 by genotype and pharmacological products). The dosage of 0.5 mg/kg for the RS 39604 was selected because its administration induced an increase of the taking of food in the nourished wild mice at libitum and remained without effect in the mutant animals for the $5\text{-}HT_4$ receptors in comparison to the mice treated with NaCl or with different dosages of RS 39604 (0.01; 0.1; 1 and 10 mg/kg; not illustrated).

Ingestion of food by the wild mice and the mice disabled for the gene coding for the $5\text{-}HT_4$ receptor was evaluated in accordance with the test protocol described by Lucas et al., 1998. The different mice were isolated for a habituation period of three days in the presence of food and water supplied ad libitum during which the weights of the mice and of the food consumed were measured daily at the same hour. On the fourth day the mice were deprived of their food for 24 hours. The drugs were injected such as NaCl after the food deprivation period to determine the effect of the different treatments on ingestion of food. Food was reintroduced into each cage after an interval of 10 min for the other treatments. Three successive weighings of the food were then carried out 30 min, 1 h and 3 h after the reintroduction of the food.

c. Conflict Tests

The superelevated cross labyrinth is constituted by two rectangular areas (L: 57 cm, 1: 5 cm) that are fixed at a right angle (90°). One of the two areas has walls 15 cm high and is called "closed arms". The other area, without walls, is called "open arms". This device is placed on a base at a height 30 cm above the floor. After a habituation period of 30 min in the test room each animal is placed at the intersection of the two areas and filmed for 5 minutes without the testers being present. The analysis of the data consists of evaluating the number of entries and the time passed in the open arms or the closed arms by the mouse, the time passed in the center and the number of times the animal inclined its head toward the floor when it was present in the open arms (head dips).

When they were placed in the test, the mice were face-to-face with the conflict between the exploration of a new environment and the fear of open spaces and height. Factorial analyses give evidence of two types of behavior: The one associated with anxiety and the other associated with motor activity (Brunner et al., 1999). It is commonly known that anxious animals return more frequently and remain longer in the closed arms and inversely for the open arms because mice are nocturnal animals.

The open field is an area 43.2×.times.43.2 cm whose walls have a height of 30 cm. Infrared sensors are arranged on the four sides at a distance of 1.5 cm from each other and are thus adapted to the size of the mice. The recording of the distance traveled is carried out by software (MED Associates Activity Monitor) for 30 min starting from the moment at which the animal is placed in the center of the test device. This protocol is repeated on three consecutive days. It is thus possible to evaluate the habituation capacity of the mice in this new environment. The testers are not present in the test room during the recording. The infrared grid permits a fine analysis of several variables to be made.

II. Results

Figure 4A:
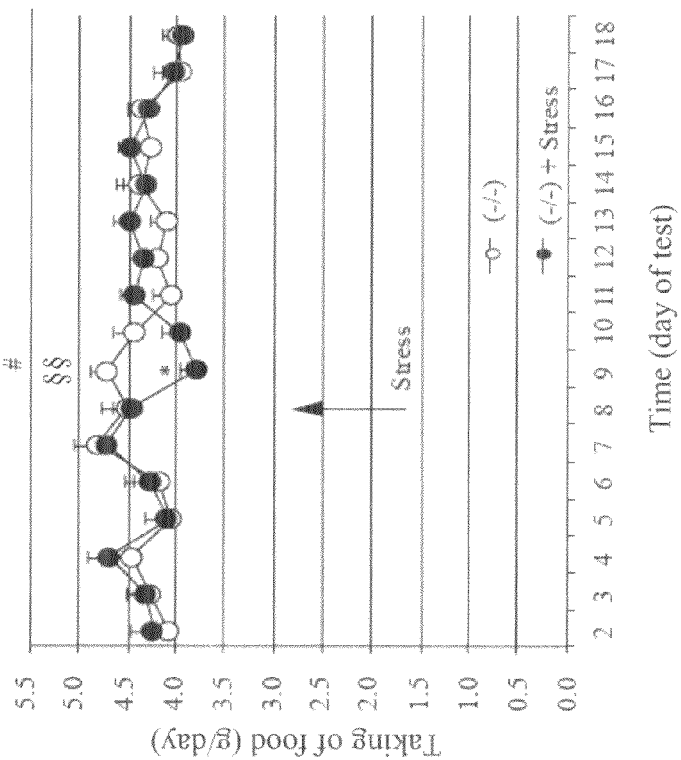
FIGS. 4a and 4b show the daily taking of food for the wild mice (FIG. 4a) and the mutants (FIG. 4b). The daily taking of food is the difference between the quantity of food evaluated during two consecutive days. The data is evaluated during a period of habituation (8 days) and of recovery (10 days). The sharp strain of constraint of 110 min is applied on the $8^{th}$ day (arrow). This forced immobilization induced a decrease of the taking of food in the wild mice during two days of the recovery period (FIG. 4a).

II.1. Hyposensitivity of the Mice Deprives of the 5-$HT_4$ Receptor in Anorexigenic Stress: Constraint Stress or Forced Immobilization Constraint stress, proposed as an experimental model for the study of anorexia (Rybkin et al., 1997, Harris et al., 2002) has been used for testing the resistance limits of mice disabled for the gene coding for the 5-$HT_4$ receptor to not consume food after stress. Ingestion of food and variations of weight gain were measured for a habituation period of 8 days and of a recovery of 10 days (FIG. 4).

During an isolation period of 8 days (habituation period) ingestion of food by the mice lacking the 5-$HT_4$ receptor was not different than that of the wild mice. Variations in their weight gain during the habituation period were less than those of the wild animals, as is indicated by the significant interaction between the genotype and the time ($F_{1,360}=2,45$; $p<0.05$). In other words, no significant variation of weight gain was detected in the mutant mice ($F_{39, 186}=0.94$) whereas it was increased in the wild mice ($F_{29, 176}=4, 45$; $p<0.001$). Ingestion of food or the changes in weight gain between the two groups of animals of the same genotype, programmed to be immobilized or not immobilized on the $8^{th}$ day, were not significantly different (FIGS. 4 a,b).

Figure 4B:
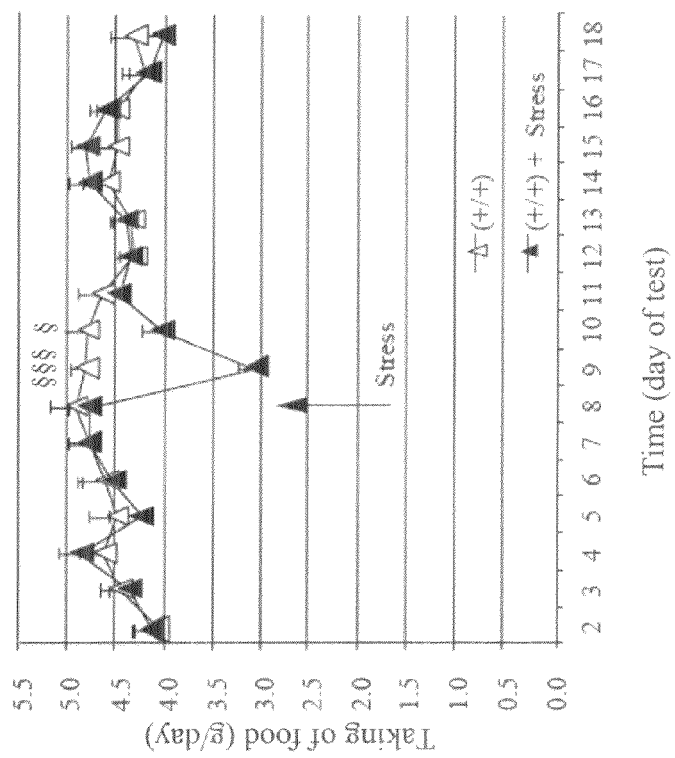

After the constraint stress the statistical analysis (repeated Anova measuring) indicated a significant effect of the stress on ingestion of food over the course of time ($_{9,567}=1\ 3, 99$; $p<0.0001$) and a significant genotype x time interaction ($F_{9,549}=2\ 0.2$, $p<0.05$). The analysis (two-way Anova) also revealed that the capacity of the constraint stress to induce a lowering of ingestion of food depends on the genotype the first 24 h following the stress ($F_{1,61}=6, 73$; $p<0.05$). Consumption of food was significantly reduced in the wild mice (−36.4%, FIG. 4a) and, in a lesser amplitude, in the mutant mice (−19.6%, FIG. 4b) in comparison to the non-stressed mice of the same genotype. A more detailed analysis indicated that the mice deprived of the 5-$HT_4$ receptor consumed significantly more food than the wild mice 24 h after the immobilization (+24%, $p<0.05$). After 48 h only the wild mice consumed even less food relative to the control animals (−16.4%, FIG. 4a). No significant effect of the stress on ingestion of food by the mutant mice was detected 48 h after the forced immobilization (FIG. 4b).

Figures 4C, 4D:
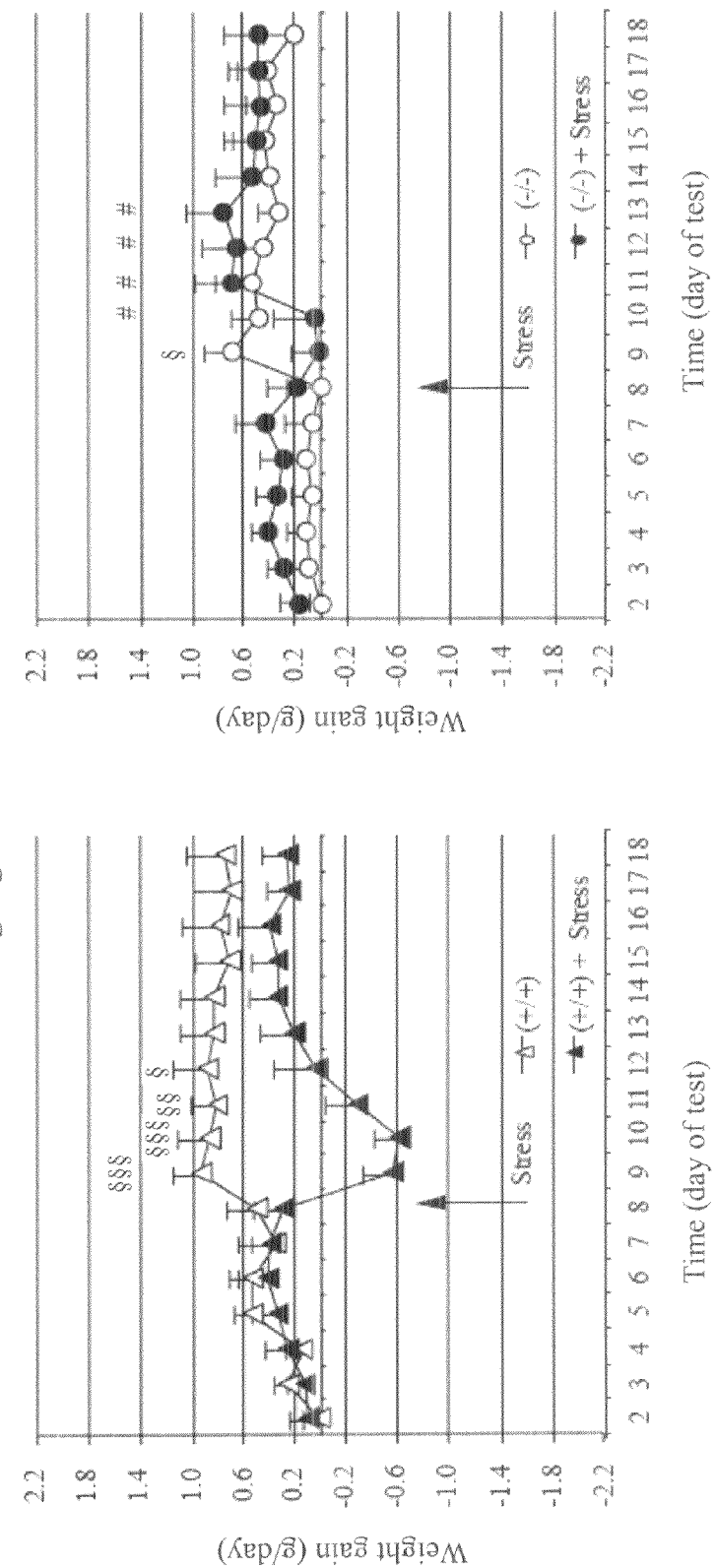
FIGS. 4c and 4d show the daily variations of the weight gain in wild mice (FIG. 4c) and in mutants (FIG. 4c) from the first day of isolation (9:00 of the illuminated part of the cycle) of the habituation period. The stress of constraint caused significant decreases in the weight gain in the wild mice (c) but much less or not at all in the mutant mice (d). The data is the averages±the standard deviation from the average (g./day) of groups of non-stressed (n=14) or constrained (n=16) wild mice and of mutant animals without stress (n=17) or immobilized (n=16). The significant differences between the stressed animals or not-stressed animals are noted by §§§$p<0.0001$; §§$p<0.001$; §$p<0.05$. The significant differences between the two genotypes are marked by * $p<0.05$ and the significant interactions genotype x stress By $p<0.05$.

In a parallel manner, the statistical analysis (Anova, repeated measurements) indicated a significant effect of the stress on the variations in the weight gain over the course of time ($F_{9,522}=11, 33$; $p<0.0001$) and a significant genotype x time interaction ($F_{9,522}=2, 38$; $p<0.05$). The statistical analysis (Anova, repeated measurements) revealed that the constraint stress induces a significant lowering of weight gain in the wild mice ($F_{1,252}=5.76$, $p<0.05$, FIG. 4c) but not in the mice disabled for the gene coding for the receptor ($F_{1,270}=0.014$, FIG. 4d). A detailed statistical analysis indicated that the stress caused lowerings of weight gain in the wild mice the first 4 days of the recovery period in comparison to the control mice (FIG. 4c). On the other hand, the constraint stress had a lesser efficaciousness in the absence of the 5-$HT_4$ receptor since their weight gain remained stable and weaker in comparison to their stressed congeners during 24 h after immobilization (FIG. 4d).

Moreover, the results indicate that if the constraint stress is preceded by an injection of RS39604, antagonist of the 5-$HT_4$ receptor, after the forced immobilization of wild females, ingestion of food by the wild mice was not modified (not shown). In other words, the pharmacological inactivation of the 5-$HT_4$ receptor suppressed the anorexigenic effect of the constraint stress. In a parallel manner, the administration of RS39604 reduced the weight losses of the wild mice in comparison to the animals treated with NaCl (not shown) (Compan et al., 2003).

Figure 5:
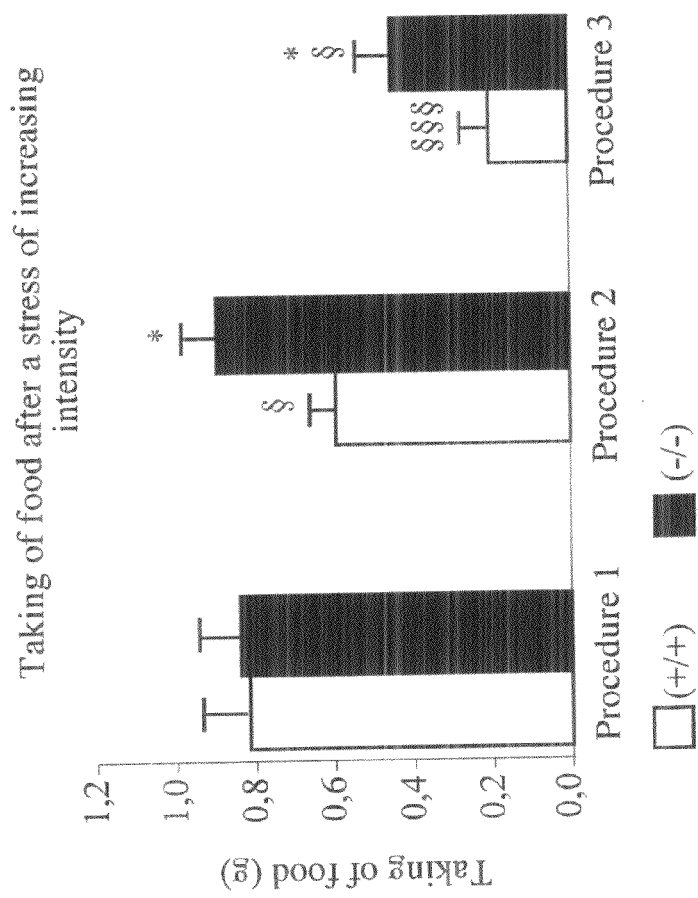
FIG. 5 shows that the mice disabled for the gene coding for the 5-HT$_4$ receptor of serotonin consume more food than the wild animals after an anorexigenic stress of increasing intensity. In other words, an experimental paradigm in which the situation becomes progressively more stressful induced a decrease of the taking of food in the wild mice whereas the anorexigenic effect was reduced in the absence of the gene coding for the 5-HT$_4$ receptor. The data represent the average±the standard deviation from the average of the taking of food (g.) in experimental contexts that are new and/or adverse for the rodents (Procedure 1: Isolation of 3 h, Procedure 2: Superelevated cross labyrinth (EPM, 5 min) and isolation of 3 h, Procedure 3: Isolation of 96 h, small incision of the tail, injection of NaCl and, EPM). The significant differences between the mice lacking the 5-HT$_4$ receptor and the wild animals are marked by * $p<0.05$. The significant differences between each of the procedures are noted by §$p<0.05$; §§$p<0.01$.

II.2. Hyposensitivity of the Mice Deprived of the 5-$HT_4$ Receptor Upon an Anorexigenic Stress of Increasing Intensity The results indicate that the adult mice deprived of the 5-$HT_4$ receptor displayed less sensitivity to the anorexigenic effects of new environments (FIG. 5). The statistical analysis showed a significant effect of the genotype ($F_{1, 47}=5, 57$; $p<0.05$) and of the procedures used ($F_{1, 47}=18, 55$; $p<0.0001$).

Transferring the mice from their customary cage to the cages for the evaluation of ingestion of food did not modify the consumption of food by the wild and the mutant mice (procedure 1, FIG. 5). The moderate stress (procedure 2), a single exposure in the superelevated cross labyrinth for 5 min, known to increase the activity of the hypothalamo-pituitary axis, induced a significant diminution of ingestion of food in the wild mice (−33.4%; $p<0.05$; n=7). This was not the case for the mutant mice (FIG. 5, n=9). The consumption of food by the mice deprived of the 5-$HT_4$ receptor was significantly more elevated than that of the wild animals after the moderate stress (+40 8, 4%; $F_{1,15}=7, 97$; $p<0.05$; n=10; FIG. 5). When using other series of animals our results indicate that an intense stress (procedure 3) involves a greater reduction of ingestion of food in the wild mice in comparison to the mice treated with procedure 2 (−70 8%; $F_{2, 19}=16, 11$; $p<0.0001$; n=8; FIG. 5). Even if ingestion of food also diminishes in the absence of the 5-$HT_4$ receptor, the mutant mice consume more food than the wild animals after a strong stress (+132%; $F_{1,22}=6.7$; $p=0.0042$; FIG. 5; n=10).

II.3. Absence or Inactivation of the 5-$HT_4$ Receptor Counteracts Inhibition of the Motivation to Consume Food Induced by Administration of MDMA or of Ecstasy The global statistical analysis of ingestion of food reveals significant effects of genotype ($F_{1,105}=4,86$; $p<0.05$), treatment ($F_{1,105}=7.24$; $p<0.001$) and time ($F_{3,315}=390,12$; $p<0.0001$). The interactions between the genotype and the treatment ($F_{3,105}=2,76$; $p<0.05$) and between the factors of time and treatment ($F_{9,315}=29,30$; $p<0.0001$) are also significant.

Figure 6A:
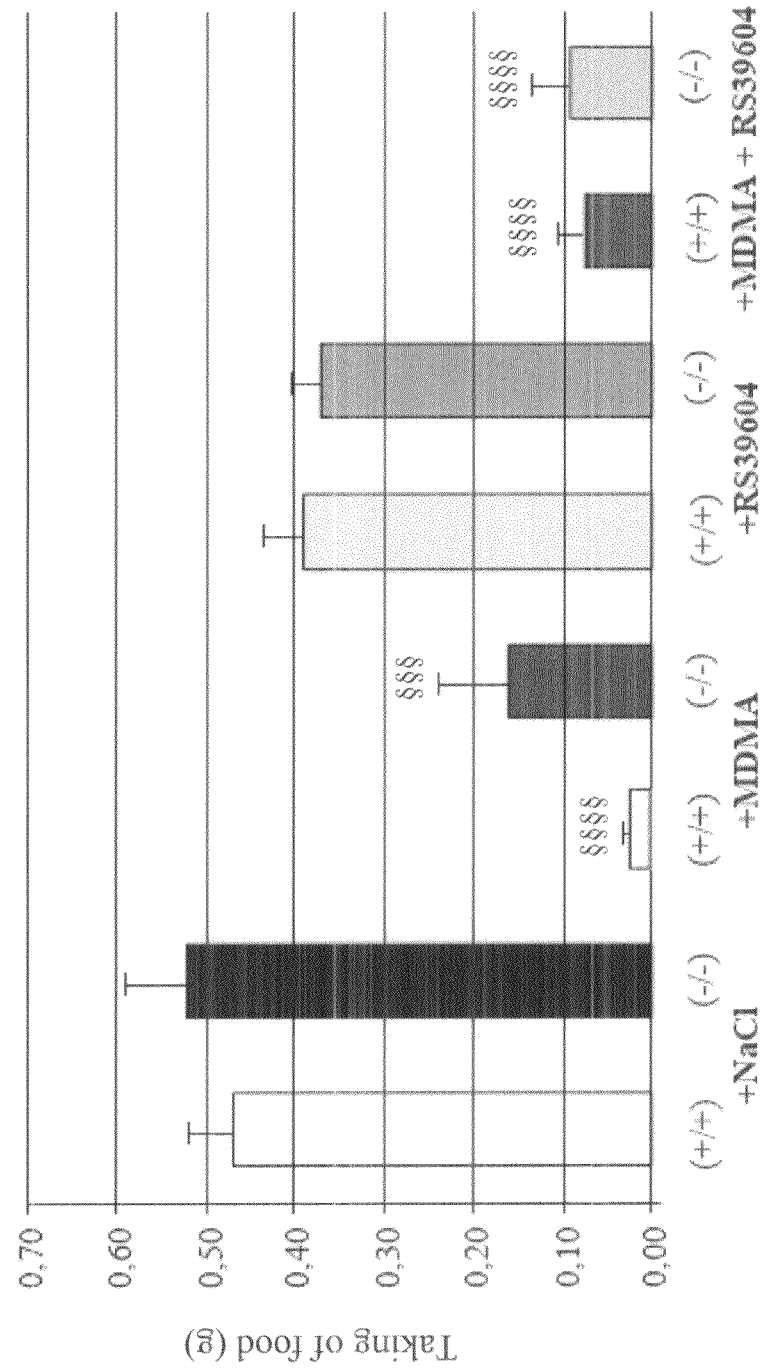
FIG. 6 shows that the mice lacking the gene coding for the 5-HT$_4$ receptor of serotonin proved to be less sensitive to the anorexigenic effects of MDMA or Ecstasy 24 after the deprivation of food. This resistance to the anorexigenic stress of Ecstasy is reproduced if it is conjointly administered with an antagonist selective for the 5-HT$_4$ receptor of serotonin (RS 39604). In other words, the sharp attenuation of the motivation to consume foods induced by the injection of Ecstasy in spite of a depravation of food for 24 h is counteracted by the absence or the inhibition of the 5-HT$_4$ receptors. The data represent the average±the standard deviation from the average of the retaking of food (g.) measured 30 min (FIG. 6A), 1 h (FIG. 6B) and 3 h (FIG. 6C) after the injection of NaCl, MDMA (10 mg/kg) and/or of RS39604 (0.5 mg/kg) in wild mice (+/+) or mice deprived of the 5-HT$_4$ receptor (−/−). * $p<0.05$ significant effect of the genotype after a variance analysis followed by test F of Scheffé. §$p<0.05$; §§§$p<0.001$; §§§§$p<0.0001$ significant effect of the treatment by comparison with the animals of the same genotype treated by NaCl (Anova, test F of Scheffé). # $p<0.05$; $p<0.01$ significant effect of the treatment by comparison with the wild animals treated with MDMA (Anova, test F of Scheffé).
Figure 6B:
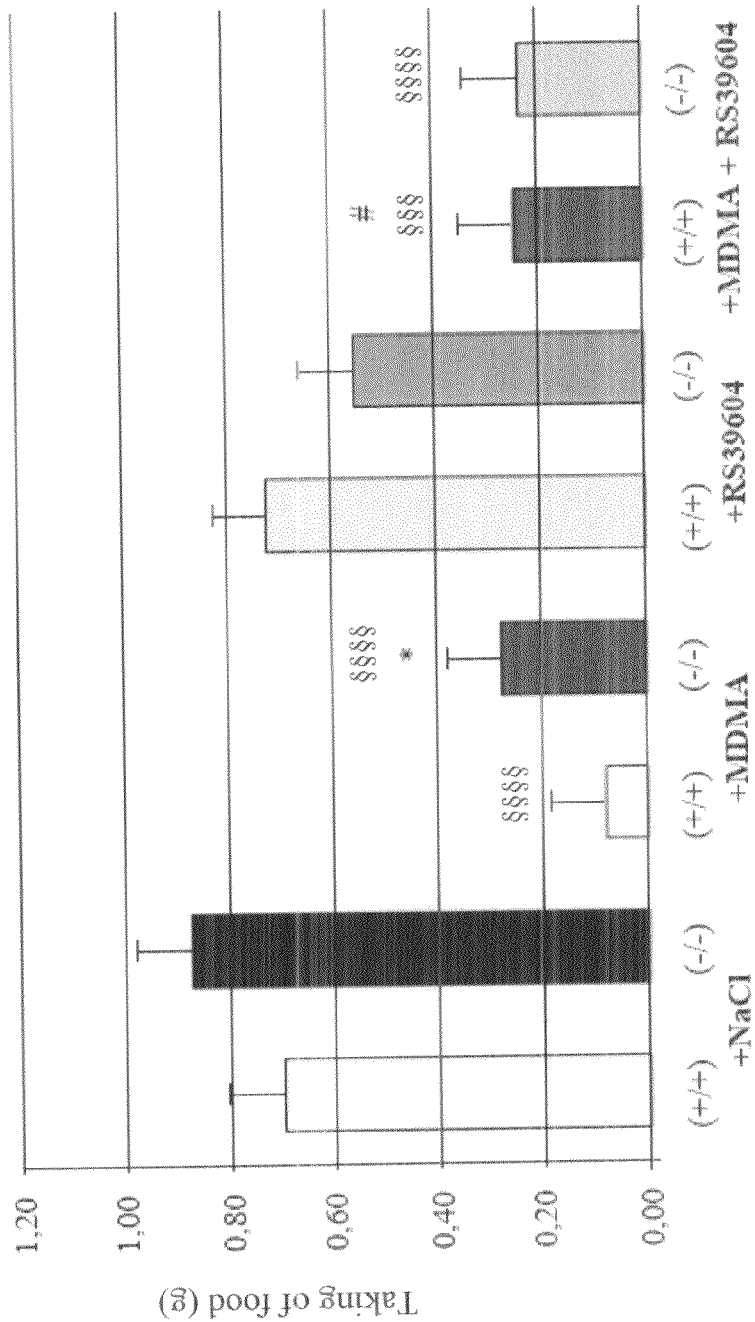
Figure 6C:
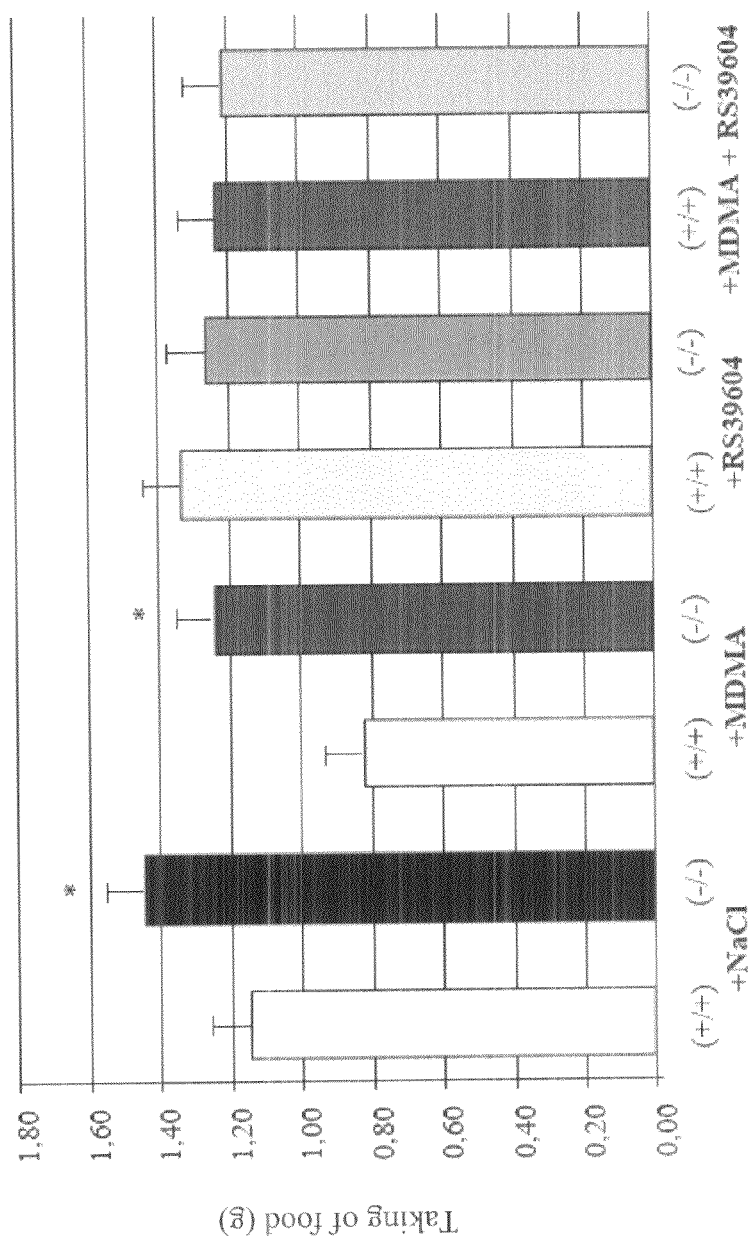

In the case of MDMA, the statistical analysis shows the significant effects of the genotype ($F_{1,59}=11.93$; $p<0.001$)

and of the treatment ($F_{1,59}=-15,78$; $p<0.001$) that vary over the course of time ($F_{3,177}=3,97$; $p<0.01$) and ($F_{3,177}=53,12$; $p<0.0001$), respectively. The results indicate that administration of MDMA induced a significant diminution of ingestion of food in the wild mice in comparison to the rodents of the same genotype treated with NaCl (FIG. 6). This effect was observed 30 min (−95.38%, FIG. 6A) and 1 h (−88.56%, FIG. 6B) after its administration and is absent at 3 h (FIG. 6C). In the mice lacking the 5-HT$_4$ receptor, compared to the mutant rodents treated with NaCl, MDMA also induces a significant diminution of ingestion of food 30 min (−69.07%, FIG. 6A) and 1 h (−68.49%, FIG. 6B) after its administration. This effect is no longer observed 3 h after the treatment of the mice (FIG. 6C). Furthermore, consumption of food in mice lacking the 5-HT$_4$ receptor is significantly more elevated 1 h (+645, 56%; $p<0.001$, FIG. 6B), and 3 h (+244, 23%; $p<0.05$, FIG. 6C) after administration of MDMA in comparison to wild animals that received the same treatment.

For RS 39604, antagonist of the 5-HT$_4$ receptor, the statistical analysis does not reveal significant genotype effects ($F_{1,63}=1, 37$) either of the treatment ($F_{1,63}=3, 93$) or of an interaction between the factors of genotype and treatment ($F_{1,63}=3, 93$) (FIG. 6).

In the case of MDMA combined with RS 39604, selective antagonist of the 5-HT$_4$ receptor, the statistical analysis shows a significant effect of the treatment ($F_{1,55}=7, 10$; $p<0.05$) over the course of time ($F_{3,165}=6, 87$; $p<0.0001$). The results indicate that the combined administration of MDMA and of RS 39 604 induced a significant diminution of ingestion of food in the wild mice in comparison to the rodents of the same genotype treated with NaCl. This effect was observed 30 min (−83, 72%, FIG. 6A) and 1 h (−64, 89%, FIG. 6B) after administration of MDMA/RS 39 604. No variation in the consumption of food was observed 3 h after the treatment of the animals (FIG. 6C). Our results are similar in the mice lacking the 5-HT$_4$ receptor. Administration of MDMA/RS 39604 significantly reduces their consumption of food 30 min (−82, 19%, FIG. 6A) and 1 h (−72, 88%, FIG. 6B) after injection of MDMA/RS 39604 and is without effect at 3 h (FIG. 6C) in comparison to mice of the same genotype. Moreover, the results reveal that ingestion of food by wild mice is significantly more elevated 1 h (+206.82%, FIG. 6B) and 3 h (+51.18%, FIG. 6C) after administration of MDMA/RS 39604 than that of wild animals that received only MDMA. This effect is not revealed in the mutant mice for the 5-HT$_4$ receptor.

Figures 7A, 7B:
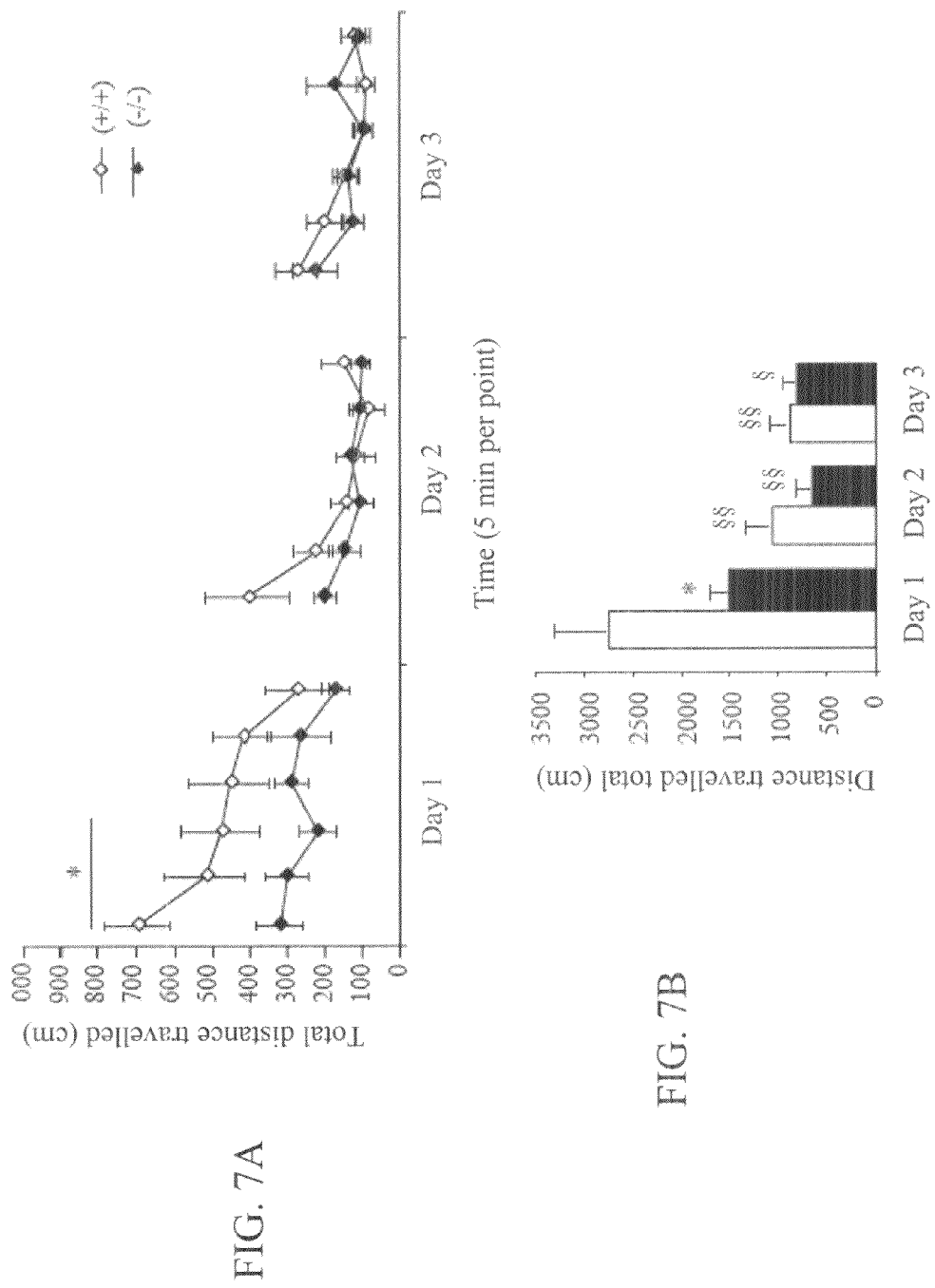
FIG. 7 shows that the mice disabled for the gene coding for the 5-HT$_4$ receptor of serotonin present deficiencies of locomotion and/or of adaptation to a new environment, here the open field. The data represents the average of the distance traversed (cm) by the wild mice (+/+, n=7) and the mutants (−/−, n=7) on the total surface (FIGS. 7a and 7b) or in the center 99 (FIGS. 7c and 7d) of the open field during 30 min and during three consecutive days (day 1 to 3). The data of FIG. 7e represents the average time passed in the center of the open field during three consecutive days.
FIG. 7f represents the average data of the vertical activity during three consecutive days. The significant differences between the genotypes are marked by *p<0.05 and between the different days of exposure by §§p<0.01 and §p<0.05.

II.4. Reaction to Novelty of the Mutant Mice for the 5-HT$_4$ Receptor in the Open Field The results presented in FIG. 7 show that the mutant mice travel significantly less distance in the open field than the wild animals only the first day of their exposure ($F_{1,14}=6.76$, $p<0.05$). No significant difference between the two genotypes was detected on the second and the third day of exposure. The mice deprived of 5-HT$_4$ receptors also remained significantly less time in the center in comparison to their wild congeners on the first ($F_{1,14}=5.50$; $p<0.05$) and the second day ($F_{1,14}=4.50$, $p<0.05$) of exposure in the open field, which suggests a more elevated level of anxiety in the mutant mice (FIG. 7e). No significant difference between the two genotypes was detected for the vertical activity (FIG. 7f), which indicates that the mutant mice would not present deficiencies of exploratory activity.

This data shows a diminution of the reactivity to novelty and/or of the locomotive activity of the mice deprived of the 5-HT$_4$ receptor in comparison to the wild mice.

II.5. Study of the Anxiety Level of the Mice Deprived of the 5-HT$_4$ Receptor

I have taken account of the coexistence of the variations of anxiety and food problems in bulimic patients and then analyzed whether variations of the state "of anxiety" of the mice deprived of the 5-HT$_4$ receptor could be connected to their persistence in consuming food in spite of the application of an anorexigenic stress.

Figure 8A:
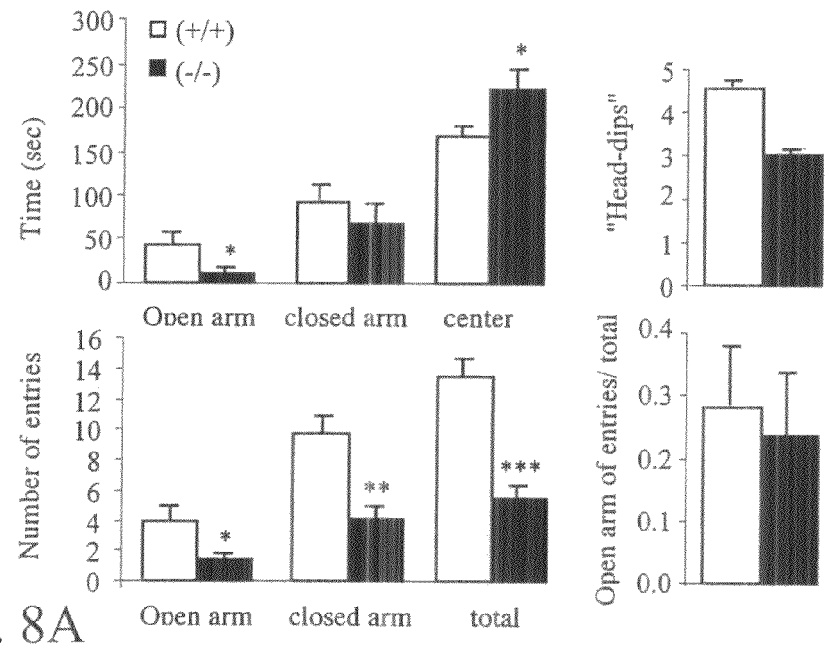
FIG. 8 shows that the mice disabled for the gene coding for the 5-HT$_4$ receptor of serotonin are less reactive to the superelevated cross labyrinth (EPM) (FIG. 8a) whereas in a context of super-induced stress the mutant mice approved to be more anxious (FIG. 8b). In the EPM without other added stress the mice remain for less time in the open arms (FIG. 8a) and were less reactive than the control animals because the numbers of entries in all the compartments of the EPM are very significantly reduced in the absence of the 5-HT$_4$ receptor (average±the standard deviation from the average, n=8-9 by genotype, reproduced three times in different laboratories). In a context of super-induced stresses the mutant mice began to react to the new environment and displayed a more anxious behavior than their wild congeners because they remained and entered less frequently in the open arms (average±the standard deviation from the average, n=18-19 by genotype). The significant differences between the genotypes are marked by *p<0.05 (Anova).
Figure 8B:
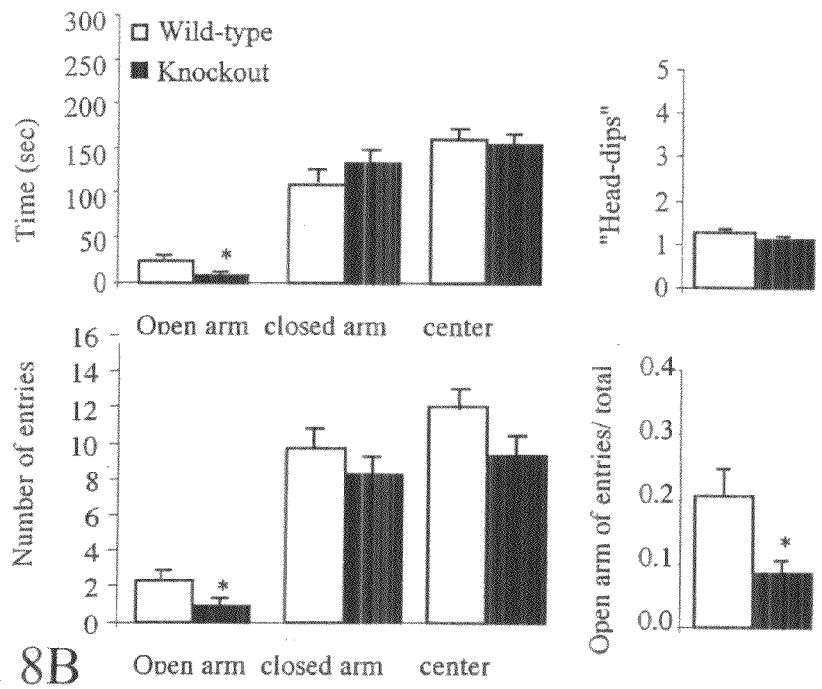

I used the superelevated cross labyrinth for this purpose, constituted by areas or closed and open arms. The more the rodents pass and enter into the closed arms the more they are considered as "anxious". The principal result indicates that procedure 3 (strong stress) induced a significant elevation of the time spent or of the number of entries into the closed arms in comparison to procedure 2 (moderate stress) (FIG. 8). Only the number of head dips, which is an index of the exploratory activity, significantly diminishes after procedure 3 in comparison to procedure 2 in the wild mice (FIG. 8). These results suggest that the mice deprived of the 5-HT$_4$ receptor present a more elevated level "of anxiety" in an adverse situation (procedure 3) relative to the wild mice.

Furthermore, significant diminution of the total number of entries into the open and closed arms by the mutant mice in the case of procedure 2 (labyrinth only) relative to wild mice suggests a lowering of their locomotive activity and/or a deficiency in adapting to novelty.

The study of the alimentary behavior under the influence of stress does not seem to be able to be envisaged without considering the influence of locomotive activity. Its increase can be associated with more elevated energetic needs and thus with a stronger consumption of food and inversely.

The data obtained during the study of the reaction to novelty (II.4. above) associated with the data obtained by using the superelevated cross labyrinth suggests that the stimulation of the 5-HT$_4$ receptor is associated with increases in locomotive activity and/or a non-adapted increase in reactivity faced with new environments. This belief reinforces that of the involvement of the 5-HT$_4$ receptor in addictions.

III. Discussion

Three types of molecular mechanisms are capable of conferring a resistance to anorexigenic stresses for mice deprived of the 5-HT$_4$ receptor.

III.1. Inability of Serotoninergic Systems to Adapt to Stress to Sufficiently Inhibit Ingestion of Food by Mutant Mice I then gave special weight to the belief of a deficiency of the serotoninergic transmission after the application of a stress in the absence of the 5-HT$_4$ receptor. The forced immobilization caused an elevation of the rates of extracellular 5-hydroxyindol acetic acid (5-HIAA) solely in the wild mice. In other words, the rates of the main metabolite of 5-HT remain unchanged in the absence of the 5-HT$_4$ receptor.

Figure 9:
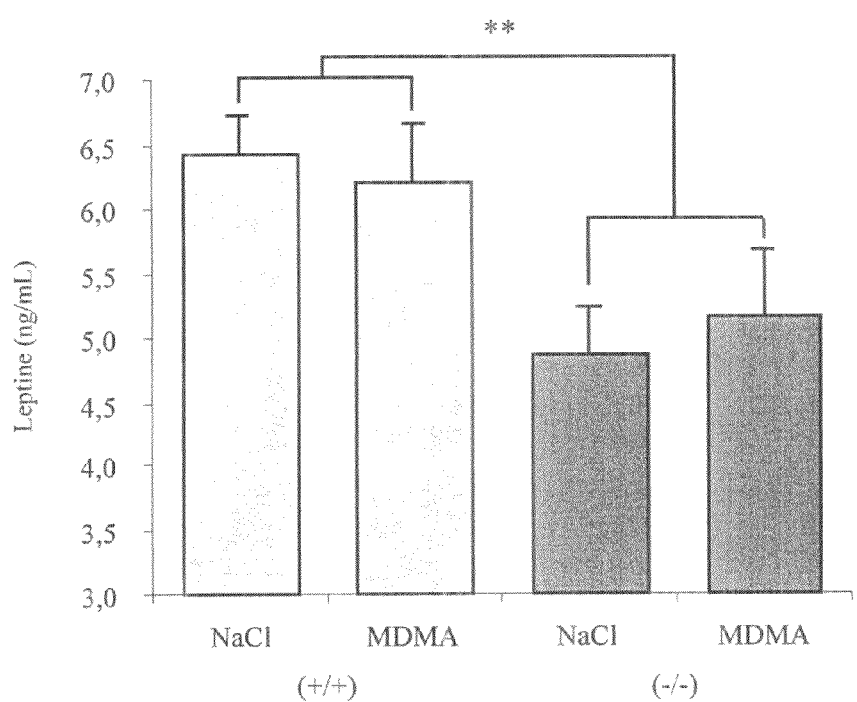
FIG. 9 shows that the absence of the gene coding for the 5-HT$_4$ receptor of serotonin induced a reduction of the rates of leptine. The data represents the average±the standard deviation from the average of the leptine rates of the plasma expressed in ng/mL after the administration of NaCl (0.9%) or of MDMA (10 mg/kg) in the wild (+/+) or the disabled (−/−) mice for the gene coding for the 5-HT$_4$ receptor, aged six to 10 months on the average. **p<0.01 significant effect of the genotype after a variance analysis (ANOVA) followed by an F test of Scheffé.

The hyposensitivity of the mutant mice to an anorexigenic stress might therefore be based on the absence of a modification of the rates of extracellular 5-HIAA (FIG. 9).

III.2. Augmentation of the Expression of the mRNA's Coding for the Peptide CART in the Mutant Mice Augmentation of the expression of the mRNA's coding for the peptide CART (cocaine—amphetamine-related transcripts, experimental MDMA paradigm) observed in the mutant mice in the nuclei accumbens and/or in the hypothalamic nuclei in comparison with the wild mice (not shown) permits the formulation of the following belief: The set of the ligands of the 5-HT$_4$ receptor is capable of controlling consumption of food by virtue of the fact of the control of the expression of the CART peptide.

Administration of this peptide can induce anorexigenic and orexigenic affects in accordance with its administration in the lateral ventricles or in the nuclei of the hypothalamus.

III.3. Lowerings of the Rates of Leptine Detected in the Mutant Mice

Lowerings of the rate of leptine detected in the mice disabled for the 5-HT$_4$ receptor (FIG. 9, experimental MDMA paradigms) allows the proposal that the ligands of the 5-HT$_4$ receptors can regulate the variations in the consumption of food and in weight by the control of the rates of leptine.

The statistical analysis of the variations of the rates of leptine did not reveal a significant effect of the treatment with MDMA (p=0.95). These results indicate that a single administration of MDMA does not modify the rates of leptine in the wild or in the mutant mice (FIG. 9).

In the absence of the gene coding for the 5-HT$_4$ receptor the statistical analysis of the variations of the leptine rates reveals a significant genotype effect ($F_{1,27}$=10,42; p<0.01). These results show that the leptine rates are significantly less elevated in the mice disabled for the gene coding for the 5-HT$_4$ receptor in comparison to the wild animals (−21%) as the use of test F of Scheffé also indicates (p<0.01) (FIG. 9).

III.4. Conclusion

The anorexigenic effect of stress could be based on a cascade of events of which the first link is an increase in the activity of the hypothalamo-pituitary axis. An elevation of the transmission of monoamines (5-HT and DA) that inhibits the taking of food follows. In the current state of knowledge none of the receptors of 5-HT was shown to represent a molecular element responsible for the anorexigenic effect of stress with the exception of a single pharmacological study on the 5-HT$_{2A/2C}$ receptor (Grignaschi et al., 1993). It was quite recently reported that the weight of mutant mice for the 5-HT$_2$ receptor diminishes in a manner comparable to that of wild mice as a consequence of the repeated application of constraint stress (Clifton et al., 2003).

The behavioral results demonstrate a hyposensitivity of the mice lacking the 5-HT$_4$ receptor to an anorexigenic stress, confirming the inhibitory control of 5-HT on the consumption of food. They support the hypothesis of the contribution of 5-HT in the anorexigenic effect of stress of which the 5-HT$_4$ receptor is one of the mediators. Taking into account the modifications of the serotoninergic parameters in the NAc and the hypothalamus in the absence of the 5-HT$_4$ receptor, it is then possible that stress does not increase the release of 5-HT in a proportion sufficient to diminish the taking of food of mutant mice after stress.

Some data is in favor of a positive control of the release of the 5-HT as a consequence of the activation of the 5-HT$_4$ receptor. The stimulation of the 5-HT$_4$ receptor induces a closure of the ionic channels of potassium (Bockaert et al., 1998), which is capable of maintaining the excitability of the neurons and increasing the release of neuromediators. In agreement with this data, stimulation of the 5-HT$_4$ receptor leads to an elevation of the rates of extracellular 5-HT in the hippocampus (Ge & Barnes, 1997). In the base conditions (without stress) this data shows an elevation of the 5-HIAA/5-HT ratio in the hypothalamus and the NAc, which suggests an alteration of the metabolism of the 5-HT in the absence of the 5-HT$_4$ receptor. Moreover, these results suggest that the lowering of the rates of the 5-HT in the hypothalamus after stress is not compensated in the mice deprived of the 5-HT$_4$ receptor even though the density membrane transporter of the 5-HT marked by the tritiated citalopram is stronger than in the NRD.

Interestingly, leptine, the genetic disabling of which renders mice obese, can increase the rate of renewal of the 5-HT in the hypothalamus (Calapai et al., 1999; Hastings et al., 2002) as well as the concentration of the capture transporter of the 5-HT in the frontal cortex (Charnay ea., 1999). Moreover, disabling the gene coding for leptine induces a diminution of the rates of mRNA coding for the membrane transporter of 5-HT in the NRD (Collin et al., 2000). Localization of the receptors of leptine on the serotoninergic neurons of NRD and the nucleus of the median raph of the mouse (Finn et al., 2001) represents a supplementary argument in favor of an interaction between leptine and the serotoninergic neurons. In the same experimental paradigm of the use of MDMA these results indicate that the rates of leptine are diminished in the mutant mice. Furthermore, the injection of MDMA did not induce a variation of leptinemia. This data indicates a positive control of the leptine rates as a

REFERENCES

Abbott C R. Rossi M. Wren A M. Murphy K G. Kennedy A R. Stanley S A. Zollner A N.

Morgan D G. Morgan I. Ghatei M A. Small C J. Bloom S R. (2001) Endocrinology, 142, 3457-63.

Ackerman S. Nolan L J. (1998) CNS Drugs., 9, 135-51.

Adell A. Casanovas J M. Artigas F. (1997) Neuropharmacology, 36, 735-741.

Allison D B. Mentore J L. Heo M. Chandler L P. Cappelleri J C. Infante M C. Weiden P J. (1999) J. Psychiatry, 156, 1686-96.

Amat J. Matus-Amat P. Watkins L R. Maier S F. (1998) Brain Res., 812, 113-120.

Barnes N M. & Sharp T. (1999) Neuropharmacology, 38, 1083-152.

Barsh G S. Farroq I S. O'Rahilly S. (2000) Nature, 404, 644-51.

Bockaert et al. (1997) Handbook of Experimental Pharmacology, Vol. 129. Serotonergic Neurons and 5-HT receptors in the CNS. Eds. H. G. Baumgarten and M. Gothert. Springer-Verlag Berlin Heidelberg. 439-474.

Bockaert J. Ansanay H. Letty S. Marchetti-Gauthier E. Roman F. Rondouin G. Fagni L. Soumireu-Mourat B. Dumuis A. (1998) C R Acad Sci III., 321 (2-3), 217-21.

Bockaert J. Claeysen S. Sebben M. Dumuis A. (1998) Ann N Y Acad Sci., 861, 1-15.

Bockaert J. Claeysen S. Compan V. Dumuis A. (Revue, 2003, sous presse) 5-HT$_4$ receptor in CNS functions: are they potential therapeutical targets? Drug Target.

Bonasera S J. Tecott L H. (2000) Pharmacol Ther., 88 (2): 133-42.

Bonhomme N. De Deurwaërdere P. Le Moal M. Spampinato U. (1995) Neuropharmacology, 3, 4269-279.

Bou knecht J A. Van der Gugten J. Hijzen T H. Maes R A. Hen R. Olivier B. (2001) Psychopharmacology, 153 (4), 484-90.

Brunner D. Buhot, M-C. Hen R. Hofer M. (1999) Behav Neurosci., 113, 587-601.

Calapai G. Corica F. Corsonello A. Sautebin L. Di Rosa M. Campo G M. Buemi M. Mauro V N. Caputi A P. (1999) J Clin Invest., 104, 975-82.

Carlsson L. Amos G J. Andersson B. Dre s L. Duker G. Wadstedt G. (1997) J Pharmacol Exp Ther., 282, 220-7.

Casper R C. (1998) Depress Anxiety, 8, 96-104.

Chaouloff F. (2000) J. Psychopharmacol., 14, 139-151.

Charnay Y. Cusin I. Vallet P G. Muzzin P. Rohner-Jeanrenaud F. Bouras C. (2000) Neurosci Lett., 283, 89-92. Claeysen S. Sebben M. Becamel C. Parmentier M-L. Dumuis A. Bockaert J. (2001) EMBO reports, 21, 61-67.

Clifton P G. Lee M D. Somerville E M. Kennett G A. Dourish C T. (2003) Eur J Neurosci., 17, 185-90.

Collin M. Hakansson-Ovesjo M. Misane I. Ogren S O. Meister B. (2000) Brain Res Mol Brain Res., 81, 51-61.

Compan V. Charnay Y. Daszuta A. Hen R Bockaert J. (2003) Comptes rendus de la Societe de Biologie de Paris.

Cheng C H K. Costall B. Kelly M. Naylor R J. (1994) Eur J Pharmacol., 255, 39-49. Compan V. Daszuta A. Salin P. Sebben M. Bockaert J. Dumuis A. (1996) Eur J Neurosci., 8, 2591-2598.

Compan V. Dusticier N. Nieoullon A. Daszuta-A. (1996) Synapse, 24, 87-96.

Costall B. & Naylor R J. (1997) Br J Pharamcol., 122, 1105-1118.

De Deur aerdère P. L'Hirondel M. Bonhomme N. Lucas G. Cheramy A. Spampinato U. (1997) J Neurochem., 68, 195-203.

Di Chiara G. (1995) Drug Alcohol Dépend, 38, 95-137.

Donohoe T P. (1984) Life Science, 34 (3), 203-218.

Dourish C T. Hutson P H. Kennett G A. Curzon G. (1986) Appetite, 7 Suppl, 127-40.

Dumuis A. Bouhelal R. Sebben M. Cory R. Bockaert J. (1988) Mol. Pharmacol., 34, 880-887.

Erecius L F. Dixon K D. Jiang J C. Gietsen D W. (1996) J Nutri., 226", 1722-1731."

Fairburn C G. Doll H A. Welch S L. Hay P J. Davies B A. O'Connor M E. (1998) Arch Gen Psychiatry, 55, 233-241.

Finn P D. Cunningham M J. Rickard D G. Clifton D K. Steiner R A. (2001) J Clin Endocrinol Metab., 86, 422-6.

Foltin R W. & Evans S M. (1999) Pharmacol Biochem Behav., 62, 457-64.

Fontana D J. Daniels S E. Wong E H. Clark R D. Eglen R M. (1997) Neuropharmacology, 36, 689-96.

Garro J. (1991) Br Med J., 303, 704-706.

Ge J. & Barnes N M. (1996), Br J Pharmacol, 11 7, 1475-80.

Ge J. Barnes N M. Costall B. Naylor R J. (1997) Pharmacol Biochem Behav., 58, 775-783.

Gerald C. Adham N. Kao H T. Olsen M A. Laz T M. Schetcher L E. Bard J A. Vaysse P J. Hartig P R. Branchek T A. (1995) EMBO J., 14, 2806-2815.

Godart N T. Flament M F. Lecrubier Y. Jeammet P. (2000) Eur Psychiatry., 15, 38-45.

Grignaschi G. Mantelli B. Samanin R (1993) Neurosci Lett., 152, 103-6.

Guerre-Millo M. (1997) Biomed Pharmacother., 51, 318-23.

Guy—Grand B. (1995) Obes. Res., 4, 491S-496S.

Harris R B. Mitchell T D. Simpson J. Redmann S M Jr. Youngblood B D. Ryan D H. (2002) Am J Physiol Regul Integr Comp Physiol. 282, R77-88.

Hastings J A. Wiesner G. Lambert G. Morris M J. Head G. Esler M. (2002) Regul Pept., 103, 67-7'4.

Heisler L K. Chu H M. Tecott L H. (1998) Ann N Y Acad Sci., 15: 861:74-8.

Hcebel B G. (1997) Appetite, 29, 119-133.

Inoue T. Tsuchiya K. Koyama T. (1994) Pharmacol. Biochem. Behav., 49, 911-920.

Jiang J C. & Gietzen D W. (1994) Pharmacol Biochem Behav., 47, 59-63.

Joseph M H. & Kennett G A. (1983) Brain Res., 270, 251-257.

Joubert L. Claeysen S. Sebben M. Bessis A S. Clark R D. Martin R S. Bockaert J. Dumuis A. (2002) J Biol Chem., 277, (28) 25502-11

Kelley A E. Swanson C J. (1997) Behav Brain Res., 89, 107-113.

Kennett G A. Bright F. Trail B. Blackburn T P. Sanger G J. (1997) Neuropharmacology, 36, 707-712.

Konstandi M. Johnson E. Lang M A. Malamas M. Marselos M. (2000) Pharmacol Res., 41, 341-346.

Koob G F. Nestler E J. (1997). J Neuropsychiatry Clin Neurosci., 9, 482-497.

Kristensen P. et al. (1998) Nature, 393, 72-6.

Kucksmarski R J. Flegal K M. Campbell S M. Jonhson C L. (1994) J Am Med Assoc., 272, 205-211.

Lilenfeld L R. et al., (1998) Arch Gen Psychiatry, 55, 603-610.

Lo ry C A. Rodda J E. Stafford L. Lightman Ingram C D. (2000) J. Neurosci., 20, 7728-7736.

Lucas G. Di Matteo V. De Deur aerdère P. Porras G. Martin-Ruiz R. Artigas F. Esposito E.

Spampinato U. (2001) Eur. J. Neurosci., 13, 889-890.

Lucas J. Yamamoto A. Scearce-Levie K. Saudou F. Hen R. (1998) J Neurosci., 18, 5537-5544.

Me Mahon L R. & Cunningham K A. (1999) J Pharmacol Exp Ther., 291, 300-307.

Momose K. Inui A. Asakawa A. Ueno N. Nakajima M. Fujimiya M. Kasuga M. (1999) Diabetes Obes Metab., 5, 281-284.

Morley J E. Levine A S. Ro land N E. (1983) Life Science, 32, 2169-82.

Nonogaki K. Strack A M. Dallman M F. Tecott L H. (1998) Nat Med., 4 (10), 1152-6.

Pelleymounter M A. Cullen M J. Baker M B. Hecht R. Winters D. Boone T. Collins F (1995) Science, 28; 269 (5223), 540-3.

Phillips T. J. Hen R. Crabbe J. C. (1999) Psychopharmacology 147, 5-7.

Price M L. Lucki I. (2001) J. Neurosci., 21, 2833-2841.

Rodgers R J. Haller J. Holmes A. Halasz J. Walton T J. Brain P F. (1999) Physiol. Behav, 68, 47-53

Rybkin I I. Zhou Y. Volaufova J. Smagin G N. Ryan D H. Harris R B. (1997) Am J Physiol. 273, R1612-22.

Salamone J D. Cousins M S. Snyder B J. (1997) Neurosci Biobehav Rev., 21, 341-359.

Samanin R. Garattini S. (1996) Thérapie, 51, 107-15.

Saudou F. Hen R. (1994) Medical Chemistry Research, 4, 16-84.

Scearce-Levie K. Viswanathan S S. Hen R. (1999) Psychopharmacology, 141, 154-161.

Scearce-Levie K. Co and P. Redfern C H. Conklin B R. (2001) Trends Pharmacol Sci., 22, 414-20.

Semenova T P. Ticku M K. (1992) Brain Res., 588 (2), 229-36.

Sillaber I. Montko ski A. Landgraf R. Barden N. Holsboer F. Spanagel R. (1998) Neuroscience, 85, 415-425.

Silvestre J S. Fernandez A G. Palacios J M. (1996) Eur J Pharmacol, 309, 219-222.

Stanley S A. Small C J. Murphy K G. Rayes E. Abbott C R. Seal L J. Morgan D G. Sunter D. Dakin C L. Kim M S. Hunter R. Kuhar M. Ghatei M A. Bloom S R. (2001) Brain Res., 893, 186-94.

Steward L J. Ge J. Stowe L R. Brown C. Bruton R K. Stokes P R A. Barnes N M. (1996) J. Pharm., 11 7, 55-62.

Stradford T R. Kelley A. (1997) J Neurosci., 1 7, 4434-4440.

Stradford T R. Kelley A. (1999) J Neurosci., 19, 11040-8.

Stradford T R. Swanwon C J. Kelley A. (1998) Behav Brain Res., 93, 43-50.

Taber M T. Fibiger H C. (1997) Neuroscience, 76, 1105-112.

Ulmer C. Engels P. Abdel 'Al A. Lubbert H. (1996) Naunyn-Schmied Arch. Pharmacol., 354, 210-212.

Vergoni A V. & Bertolini A. (2000) Eur J Pharmacol., 405 (1-3), 25-32.

Vickers S P. Dourish C T. Kennett G A. (2001) Neuropharmacology, 2, 200-9.

Visselman J O. Roig M. (1985) J Clin Psychiatry, 46, 118-24.
Vilaro M T. Cortès R. Gerald C. Branchek T A. Palacios J M. Mengod G. (1996) Mol Brain Res., 43, 356-360.
Waeber C. Sebben M. Nieoullon A. Bockaert J. Dumuis A. (1994) Neuropharmacology, 33, 527-541.
Yamada J. Sugimoto Y. Ujikawa M. (1999) Eur J Pharmacol., 383, 49-51.
Zahorodna A, Tokarski K, Bijak M. (2000) Pol J Pharmacol., 52 (2), 107-9.

The invention claimed is:

1. A method of treating a pathology associated with an obsessional behavior of a mammal in need thereof, wherein the pathology is anorexia, the method comprising administering a therapeutically effective amount of an antagonist of a 5-$HT_4$ receptor, an inverse agonist of a 5-$HT_4$ receptor, a pharmaceutically acceptable salt of the antagonist, or a pharmaceutically acceptable salt of the inverse agonist to the mammal to treat the mammal.

2. The method of claim 1, wherein an antagonist is administered.

3. The method of claim 2, wherein the antagonist is selected from the group consisting of
tropisetron (ICS 205 930; [(3a tropanyl)-1H-indole-3-carboxylic acid ester]),
RS 100235 (1-(8-amino-7-chloro-1,4-benzodioxan-5-yl)-3-[[3,4-dimethoxyphenyl)prop-1-yl]piperidine-4-yl]propan-1-one,
A-85380 (3-(2(S)-azetidinylmethoxy)pyridine),
GR 113808 (1-[2-(methylsulphonyl)amino]ethyl]-4-piperidinyl]methyl 1-methyl-1H-indole-3-carboxylate),
GR 125487 (1-[2-(methylsulphonyl)amino]ethyl]-4-piperidinyl]methyl-5-fluoro-2-methoxy-1H-indole-3-carboxylate),
GR 138897 ([1-[2-[methylsulphonyl)amino]-4-piperidinyl]methyl[2-(3-methyl-1,2,4-oxa-diazon-5-yl)phenyl]carbamate],
SB 203186(1-piperidinyl)ethyl 1H-indole 3-carboxylate),
SDZ 205-557 (2-methyox-4-amino-5-chlorobenzoic acid 2-(diethylamino)ethyl ester hydrochloride),
LY 353433 (1-(1-methylethyl)-N-(2-(4-((tricyclo[2-(3.3.1.1$^{3}$,7]dec-1-ylcarbonyl)amino-1-piperidinyl)ethyl)-1H-indazole-3-carboxamide),
RS 23597 (3-piperidine-1-yl)propyl-4-amino-5-chloro-2-methoxybenzoate hydrochloride),
SB 204070 (1-butyl-4-piperidinyl)methyl 8-amino-7-chloro-1,4-benzodioxan-5-carboxylate),
DAU 6285 ((endo-6-methoxy-8-methyl-8-azabicyclo[3.2.1]oct3-yl)-2,3-dihydro-2-oxo-1-H-benzimidazole-1 carboxylate hydrochloride),
SC53606 ((1-S,8-S)—N-[hexahydro-1H-pyrrolizin-1-yl)methyl]-6-chloroimidazo[1,2-a]pyridine-8-carboxamide hydrochloride),
RS67532 (1-(4-amino-5-chloro-2-(3,5-dimethoxy benzyloxyphenyl)-5-(1-piperidinyl)-1-pentanone),
SB 207266 (N-[1-.sup.nbutyl-4-piperidinyl)methyl]-3,4-dihydro-2H-[1,3]oxazino[3,2-a]indole-10-carboxamide),
RS 39604 (1-[4-amino-5-chloro-2-(3,5-dimethoxyphenyl)methyloxy]-3-[1[2-methylsulphonylamino]ethyl]piperidine-4-yl]propan-1-one),
RS 1003002 (N-2-(4-(3-(8-amino-7-chloro-2,3-dihydro-1,4-benzodioxin-5-yl)-3-oxopropyl)piperidin-1-yl)ethyl)-methanesulfonamide),
ML 10375 (2-cis-3,5-dimethylpiperidino)ethyl 4-amino-5-chloro2 methoxybenzoate),
SB 207710 (1-butyl-4-piperidinyl)methyl-8-amino-7-1,4-benzodioxan-5-carboxylate),
SB205800 (N-(1-butyl-4-piperidinyl)methyl-8-amino-7-chloro-1,4-benzodioxan-5-carboxamide),
N 3389 (N-[(1S,5R)-3,9-dimethyl-3,9-diazabicyclo[3.3.1]nonan-7-yl]-1H-indazole-3-carboxamide dihydrochloride),
and
R 50595 (4-amino-N-[(3S,4R)-1-[4,4-bis(4-fluorophenyl)butyl]-3-methoxypiperidin-4-yl]-5-chloro-2-methoxybenzamide hydrochloride).

4. The method of claim 1, wherein an inverse agonist is administered.

5. The method of claim 4, wherein the inverse agonist is selected from the group consisting of

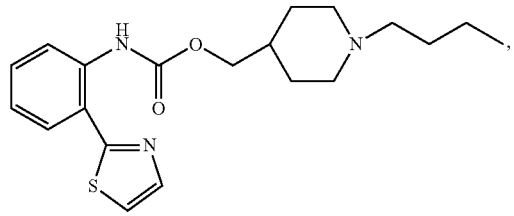

(RO 116-2617)

(1-butylpiperidin-4-yl)methyl 2,3-dihydro-1,4-benzodioxine-8-carboxylate (RO 116-0086), and
N-[(1-butylpiperidin-4-yl)methyl]-2,3-dihydro-1,4-benzodioxine-5-carboxamide (RO 116-1148).

6. The method of claim 1, wherein the mammal is a human.

* * * * *